US009533167B2

(12) United States Patent
Zurovcik

(10) Patent No.: US 9,533,167 B2
(45) Date of Patent: Jan. 3, 2017

(54) SYSTEM AND METHOD FOR MANIPULATION OF DEVICES USING MAGNETIC FIELDS

(75) Inventor: Danielle R. Zurovcik, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 251 days.

(21) Appl. No.: 13/979,528

(22) PCT Filed: Jan. 17, 2012

(86) PCT No.: PCT/US2012/021514
§ 371 (c)(1),
(2), (4) Date: Sep. 17, 2013

(87) PCT Pub. No.: WO2012/097366
PCT Pub. Date: Jul. 19, 2012

(65) Prior Publication Data
US 2014/0005522 A1 Jan. 2, 2014

Related U.S. Application Data

(60) Provisional application No. 61/432,920, filed on Jan. 14, 2011.

(51) Int. Cl.
*A61N 2/00* (2006.01)
*A61B 10/02* (2006.01)
(Continued)

(52) U.S. Cl.
CPC ............ *A61N 2/004* (2013.01); *A61B 5/055* (2013.01); *A61B 10/0233* (2013.01);
(Continued)

(58) Field of Classification Search
CPC .............. A61B 10/0233; A61B 19/22; A61B 2017/00243; A61B 2017/3407; A61B 2019/2261
See application file for complete search history.

(56) References Cited

U.S. PATENT DOCUMENTS 5,572,999 A 11/1996 Funda et al.
6,459,922 B1 10/2002 Zhang
(Continued)

OTHER PUBLICATIONS

International Search Report and Written Opinion under date of mailing of May 23, 2012 in connection with PCT/US2012/021514.

*Primary Examiner* — Baisakhi Roy
(74) *Attorney, Agent, or Firm* — Quarles & Brady LLP

(57) ABSTRACT

A system and method for manipulating devices, such as a medical implant arranged within a subject, is provided. For non-invasive manipulation of a medical implant, a subject having a non-ferromagnetic medical implant arranged therein is arranged within a system having a static magnetic field and a plurality of adjustable magnetic fields. The non-ferromagnetic medical implant includes at least one cavity and at least one ferromagnetic or ferrimagnetic material arranged within the at least one cavity. The plurality of adjustable magnetic fields of the system are controlled to induce forces on the at least one ferromagnetic or ferrimagnetic material arranged within the at least one cavity to thereby apply the induced forces to the non-ferromagnetic medical implant to effectuate a non-invasive, in vivo manipulation of the non-ferromagnetic medical implant. Other implementations include the manipulation devices such as robotic medical systems, using magnetic fields to drive the robotic medical system.

20 Claims, 12 Drawing Sheets

(51) Int. Cl.
 *A61B 5/055* (2006.01)
 *A61B 17/00* (2006.01)
 *A61B 17/34* (2006.01)

(52) U.S. Cl.
 CPC .... *A61B 34/70* (2016.02); *A61B 2017/00243* (2013.01); *A61B 2017/3407* (2013.01); *A61B 2034/732* (2016.02)

(56) References Cited

U.S. PATENT DOCUMENTS

| | | | |
|---|---|---|---|
| 6,505,062 B1* | 1/2003 | Ritter | A61B 5/066 |
| | | | 128/899 |
| 6,630,829 B1 | 10/2003 | Liu | |
| 7,510,577 B2 | 3/2009 | Moaddeb et al. | |
| 7,576,542 B1 | 8/2009 | Lvovsky | |
| 8,013,699 B2 | 9/2011 | Zimmerling | |
| 8,504,138 B1* | 8/2013 | Pivonka | A61B 1/00158 |
| | | | 600/407 |
| 8,644,951 B1* | 2/2014 | Vaidyanathan et al. | 607/116 |
| 8,855,784 B2* | 10/2014 | Lyden et al. | 607/63 |
| 2005/0020909 A1 | 1/2005 | Moctezuma de la Barrera | |
| 2006/0025713 A1* | 2/2006 | Rosengart et al. | 604/5.02 |
| 2007/0276218 A1* | 11/2007 | Yellen | 600/409 |
| 2009/0078275 A1* | 3/2009 | Hegde et al. | 128/848 |
| 2010/0244828 A1 | 9/2010 | Pines et al. | |
| 2011/0160786 A1* | 6/2011 | Stubbs et al. | 607/14 |
| 2011/0160806 A1* | 6/2011 | Lyden et al. | 607/63 |
| 2011/0299565 A1* | 12/2011 | Jester et al. | 374/161 |

* cited by examiner

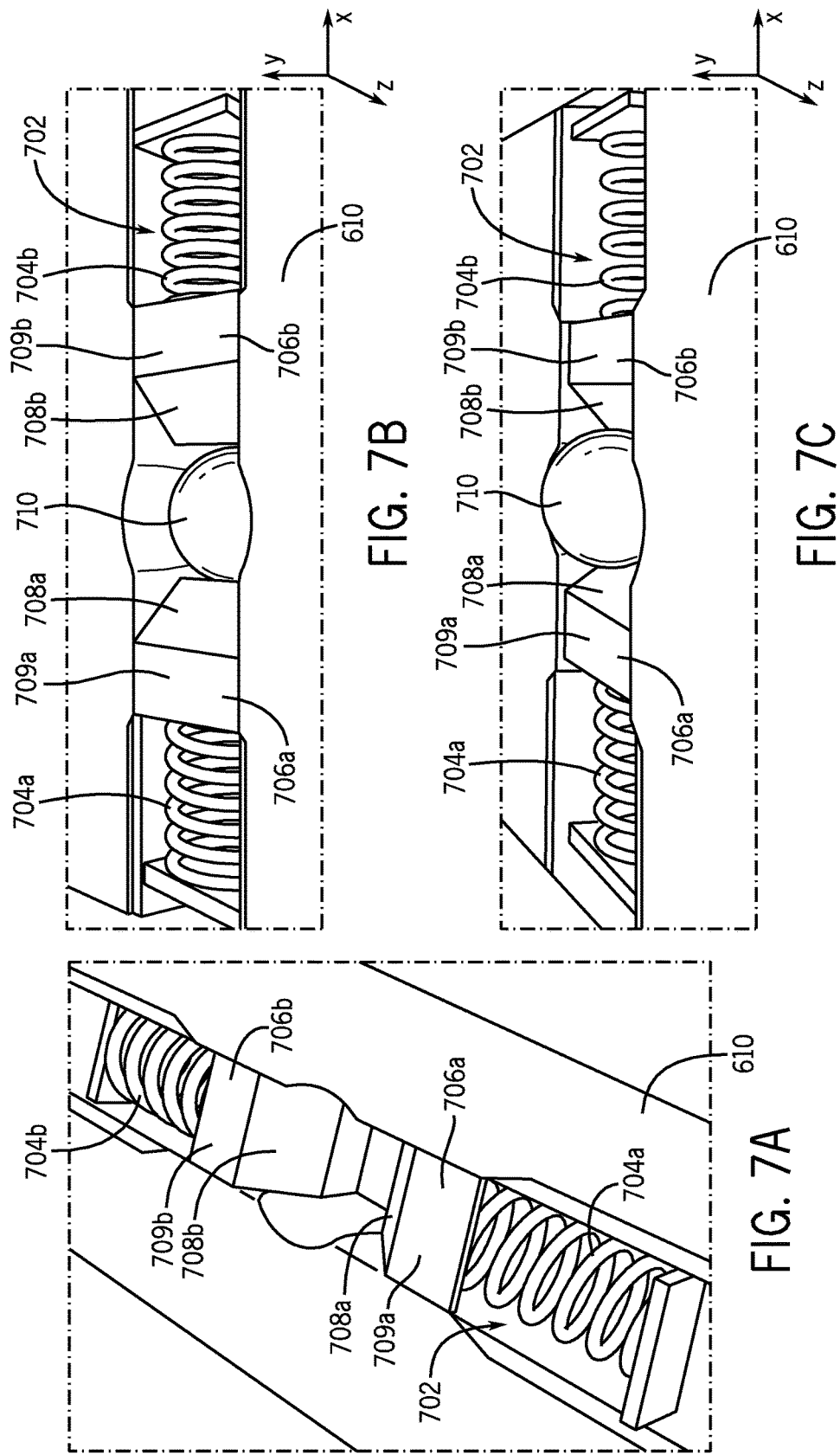

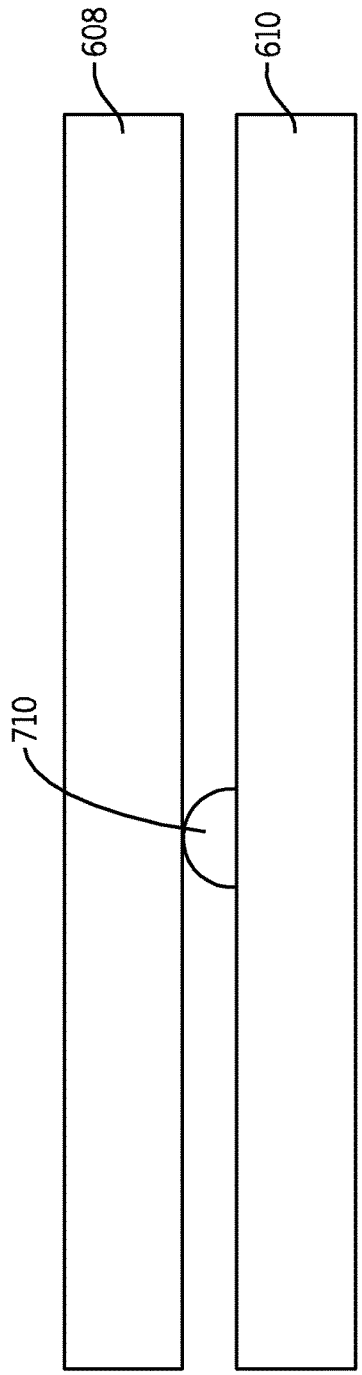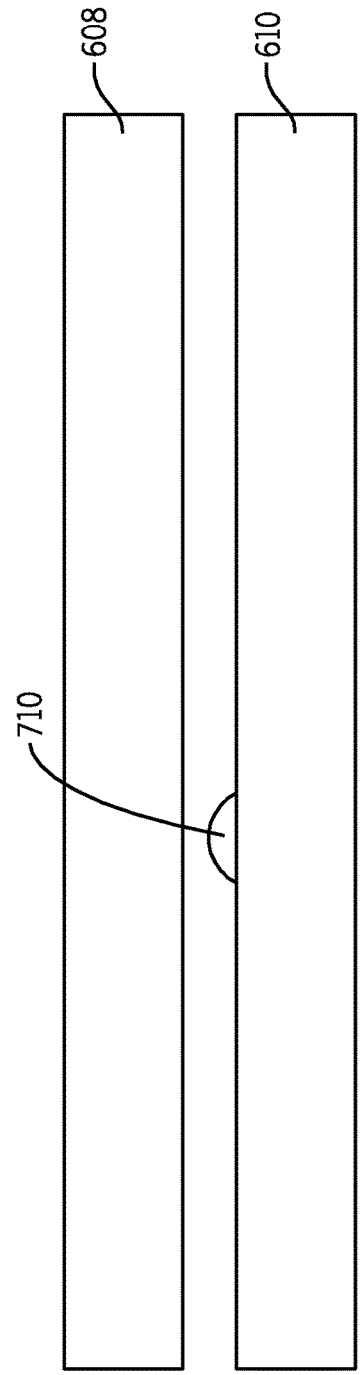

SYSTEM AND METHOD FOR MANIPULATION OF DEVICES USING MAGNETIC FIELDS

CROSS REFERENCE TO RELATED APPLICATIONS

This application represents the national stage entry of PCT International Application No. PCT/US2012/021514 filed on Jan. 17, 2012, and claims the benefit of U.S. Provisional Application Ser. No. 61/432,920 filed Jan. 14, 2011. The disclosure of each of these applications is incorporated by reference for all purposes as if set forth in their entirety herein.

STATEMENT REGARDING FEDERALLY SPONSORED RESEARCH

This invention was made with Government support under Grant No. R01 HL073647 awarded by the National Institutes of Health. The Government has certain rights in the invention.

BACKGROUND OF THE INVENTION

The field of the invention relates to systems and methods for manipulating devices, such as in vivo control of implanted devices, and, in particular, relates to systems and methods for using magnetic resonance systems to manipulate devices.

Medical implants are a multi-billion dollar industry, spanning the gamut from bone screws to pacemakers. Generally, medical implants are positioned, deployed, or otherwise implanted in a patient as part of a surgical procedure. Unfortunately, whether to reposition a bone screw or replace a power source of a pacemaker, subsequent interventional or surgical procedures are often associated with many medical implants. This is particularly true for medical implants utilized in therapeutic procedures. For example, in orthopedics, many implants may need to be adjusted or replaced as part of the progressing therapy, which typically requires some level of surgical or interventional procedure to adjust or replace the orthopedic implant. Of course, each surgical or interventional procedure undesirably subjects the patient to additional trauma and increases the general cost of the medical care.

Accordingly, substantial efforts have been made in an attempt to reduce the need to perform surgical or other interventions to adjust, configure, or otherwise maintain medical implants after initial deployment of the surgical implant. For example, substantial research and development has been made to enable wireless communications between implants and external processing systems. Additionally, substantial research and development has been made to facilitate external power and/or recharging of implants utilizing a power source, such as inductive power coupling and the like. Unfortunately, given the mechanical nature of medical implants, interventional or other surgical access to the device is often required, for example, to re-deploy a device that has moved from the original deployment position, to adjust a device to a next stage of a therapeutic cycle, or to otherwise maintain or correct the medical device.

Therefore, it would be desirable to have a system and method for further reducing the need for interventional or other surgical access to an implanted medical device, particularly, to effectuate re-deployment of a device that has moved from the original deployment position, to adjust a device to a next stage of a therapeutic cycle, or to otherwise maintain or correct the medical device.

SUMMARY OF THE INVENTION

The present invention overcomes the aforementioned drawbacks by providing a system and method for the manipulation of devices using magnetic fields as the driving force. More particularly, the present invention provides a system and method for the non-invasive, in vivo manipulation of medical implants within a subject using magnetic fields and gradients, such as available in traditional magnetic resonance imaging (MRI) systems. To overcome a wide variety of problems with directly manipulating ferromagnetic materials fixedly integrated in a medical device or ferromagnetic components affixed to a medical device, the present invention utilizes a ferromagnetic sphere arranged in a cavity formed in the medical device. Accordingly, the ferromagnetic sphere can be freely controlled within the cavity to effectuate the desired manipulation of the associated medical device.

In accordance with one aspect of the invention, a magnetic resonance imaging (MRI) system is disclosed. The MRI system includes a magnet system configured to generate a polarizing magnetic field about at least a portion of a subject arranged in the MRI system. The subject includes a non-ferromagnetic medical implant arranged therein and including at least one cavity and at least one ferromagnetic material arranged within the at least one cavity. The MRI system also includes a plurality of gradient coils configured to apply a gradient field to the polarizing magnetic field and a radio frequency (RF) system configured to apply an excitation field to the subject and acquire MR image data therefrom. The MRI system includes a computer programmed to carry out the steps of performing a medical imaging process to acquire MR image data to determine therefrom at least one of a location and an orientation of the non-ferromagnetic medical implant arranged within the subject. The computer is further programmed to carry out the steps of controlling the plurality of gradient coils and RF system to induce forces on the at least one ferromagnetic material arranged within the at least one cavity to thereby apply the induced forces to the non-ferromagnetic medical implant to effectuate a non-invasive, in vivo manipulation of the non-ferromagnetic medical implant.

In accordance with another aspect of the invention, a method for non-invasively manipulating a medical implant arranged within a subject is disclosed. A subject having a non-ferromagnetic medical implant arranged therein is arranged within a system having a static magnetic field and a plurality of adjustable magnetic fields. The non-ferromagnetic medical implant includes at least one cavity and at least one ferromagnetic material arranged within the at least one cavity. The plurality of adjustable magnetic fields of the system are controlled to induce forces on the at least one ferromagnetic material arranged within the at least one cavity to thereby apply the induced forces to the non-ferromagnetic medical implant to effectuate a non-invasive, in vivo manipulation of the non-ferromagnetic medical implant.

The foregoing and other aspects of the invention will be made apparent from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and specification as a whole for interpreting the scope of the invention.

BRIEF DESCRIPTION OF THE DRAWINGS

FIGS. 7A, 7B, and 7C are illustrations showing the internal components of a brake housing that may be incorporated into a machine to control a movement of a carriage or other moveable object that it is attached thereto.

FIG. 8A is a side view of a linear guide rail and a brake housing showing a sphere of the brake housing pressing against a lower surface of the linear guide rail.

FIG. 8B is a side view of a linear guide rail and a brake housing showing a sphere of the brake housing withdrawn from a lower surface of the linear guide rail.

DESCRIPTION OF THE PREFERRED EMBODIMENT

A common use of magnetic energy in medicine is magnetic resonance imaging (MRI). MRI scanners have a central, powerful, static magnetic field to align the nuclear magnetization of the atoms being imaged. To create an image, radio frequency (RF) fields alter the alignment of this magnetization to produce signals detectable by the scanner. Additional gradient magnetic fields can also be applied across the central field to gain further data for improving image quality.

More particularly, when a substance such as human tissue is subjected to a uniform magnetic field (polarizing field, $B_0$), the individual magnetic moments of the excited nuclei in the tissue attempt to align with this polarizing field, but precess about it in random order at their characteristic Larmor frequency. If the substance, or tissue, is subjected to an RF pulse that is perpendicular to the polarizing field and at the Larmor frequency, the net aligned moment, $M_z$, is rotated, or "tipped", out of alignment with the polarized field to produce a net transverse magnetic moment $M_t$. A signal is emitted by the excited nuclei or "spins", after the excitation RF signal is terminated, and their signal may be received and processed to form an image.

When utilizing these "MR" signals to produce images, magnetic field gradients ($G_x$, $G_y$, and $G_z$) are employed for image slice selection, since the characteristic Larmor frequency is dependent on the applied magnetic field. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Figure 1:
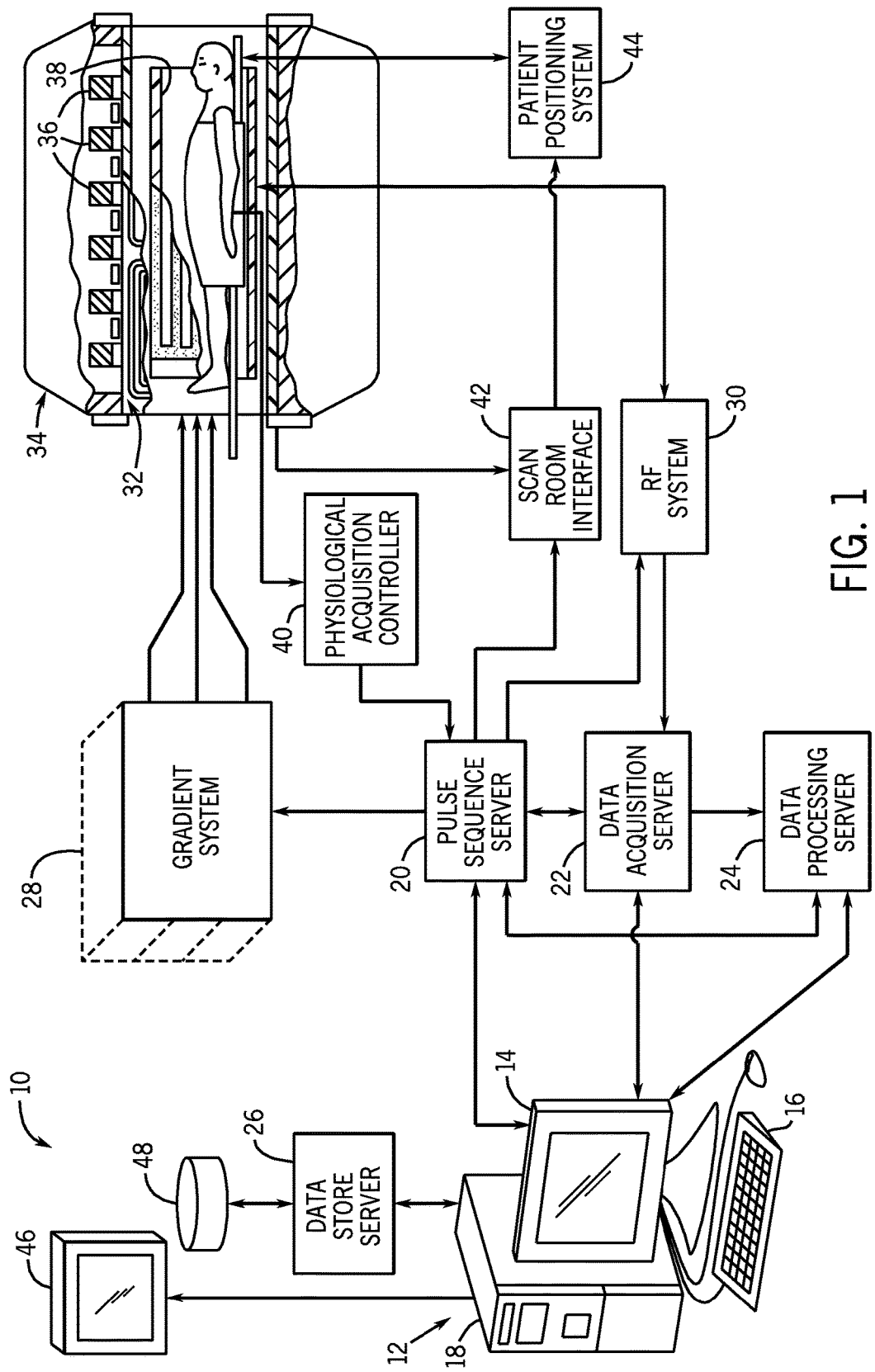
FIG. 1 is a block diagram of an MRI system that employs the present invention.

Referring to FIG. 1, the present invention may be employed using an MRI system 10. The MRI system 10 includes a workstation 12 having a display 14 and a keyboard 16. The workstation 12 includes a processor 18 that is a commercially available, programmable machine running a commercially available operating system. The workstation 12 provides the operator interface that enables scan prescriptions to be entered into the MRI system 10. The workstation 12 is coupled to, for example, four servers including a pulse sequence server 20, a data acquisition server 22, a data processing server 24, and a data storage server 26. The workstation 12 and each server 20, 22, 24, and 26 are connected to communicate with each other.

The pulse sequence server 20 functions in response to instructions downloaded from the workstation 12 to operate a gradient system 28 and an RF system 30. Gradient waveforms necessary to perform the prescribed scan are produced and applied to the gradient system 28 that excites gradient coils in an assembly 32 to produce the magnetic field gradients $G_x$, $G_y$, and $G_z$ used for position encoding MR signals. The gradient coil assembly 32 forms part of a magnet assembly 34 that includes a polarizing magnet 36 and a whole-body RF coil 38.

RF excitation waveforms are applied to the RF coil 38 by the RF system 30 to perform the prescribed magnetic resonance pulse sequence. Responsive MR signals detected by the RF coil 38 or a separate local coil (not shown in FIG. 1) are received by the RF system 30, amplified, demodulated, filtered, and digitized under direction of commands produced by the pulse sequence server 20. As will be described in detail with respect to FIG. 2, the RF system 30 includes an RF transmitter for producing a wide variety of RF pulses used in MR pulse sequences, which is responsive to the scan prescription and direction from the pulse sequence server 20 to produce RF pulses of the desired frequency, phase, and pulse amplitude waveform. The generated RF pulses may be applied to the whole body RF coil 38 or to one or more local coils or coil arrays (not shown in FIG. 1).

The RF system 30 also includes one or more RF receiver channels. Each RF receiver channel includes an RF amplifier that amplifies the MR signal received by the coil to which it is connected and a detector that detects and digitizes the I and Q quadrature components of the received MR signal. The magnitude (M) of the received MR signal may thus be determined at any sampled point by the square root of the sum of the squares of the I and Q components:

$$M = \sqrt{I^2 + Q^2},$$ Eqn. 1.

and the phase of the received MR signal may also be determined:

$$\phi = \tan^{-1} Q/I. \qquad \text{Eqn. 2.}$$

The pulse sequence server 20 also optionally receives patient data from a physiological acquisition controller 40. The physiological acquisition controller 40 receives signals from a number of different sensors connected to the patient, such as ECG signals from electrodes or respiratory signals from a bellows. Such signals are typically used by the pulse sequence server 20 to synchronize, or "gate", the performance of the scan with the subject's respiration, heart beat, or the like.

The pulse sequence server 20 also connects to a scan room interface circuit 42 that receives signals from various sensors associated with the condition of the patient and the magnet system. It is also through the scan room interface circuit 42 that a patient positioning system 44 receives commands to move the patient to desired positions during the scan.

The digitized MR signal samples produced by the RF system 30 are received by the data acquisition server 22. The data acquisition server 22 operates in response to instructions downloaded from the workstation 12 to receive the real-time MR data and provide buffer storage such that no data is lost by data overrun. In some scans, the data acquisition server 22 does little more than pass the acquired MR data to the data processor server 24. However, in scans that require information derived from acquired MR data to control the further performance of the scan, the data acquisition server 22 is programmed to produce such information and convey it to the pulse sequence server 20. For example, during prescans, MR data is acquired and used to calibrate the pulse sequence performed by the pulse sequence server 20. Also, navigator signals may be acquired during a scan and used to adjust RF or gradient system operating parameters or to control the view order in which k-space is sampled. And, the data acquisition server 22 may be employed to process MR signals used to detect the arrival of contrast agent in an MRA scan. In all these examples, the data acquisition server 22 acquires MR data and processes it in real-time to produce information that is used to control the scan.

The data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a backprojection image reconstruction of acquired MR data, the calculation of functional MR images, the calculation of motion or flow images, and the like.

Images reconstructed by the data processing server 24 are conveyed back to the workstation 12 where they are stored. Real-time images are stored in a database memory cache (not shown) from which they may be output to the display 14 or a display 46 that is located near the magnet assembly 34 for use by attending physicians. Batch mode images or selected real time images are stored in a host database on disc storage 48. When such images have been reconstructed and transferred to storage, the data processing server 24 notifies the data storage server 26 on the workstation 12. The workstation 12 may be used by an operator to archive the images, produce films, or send the images via a network to other facilities.

Figure 2:
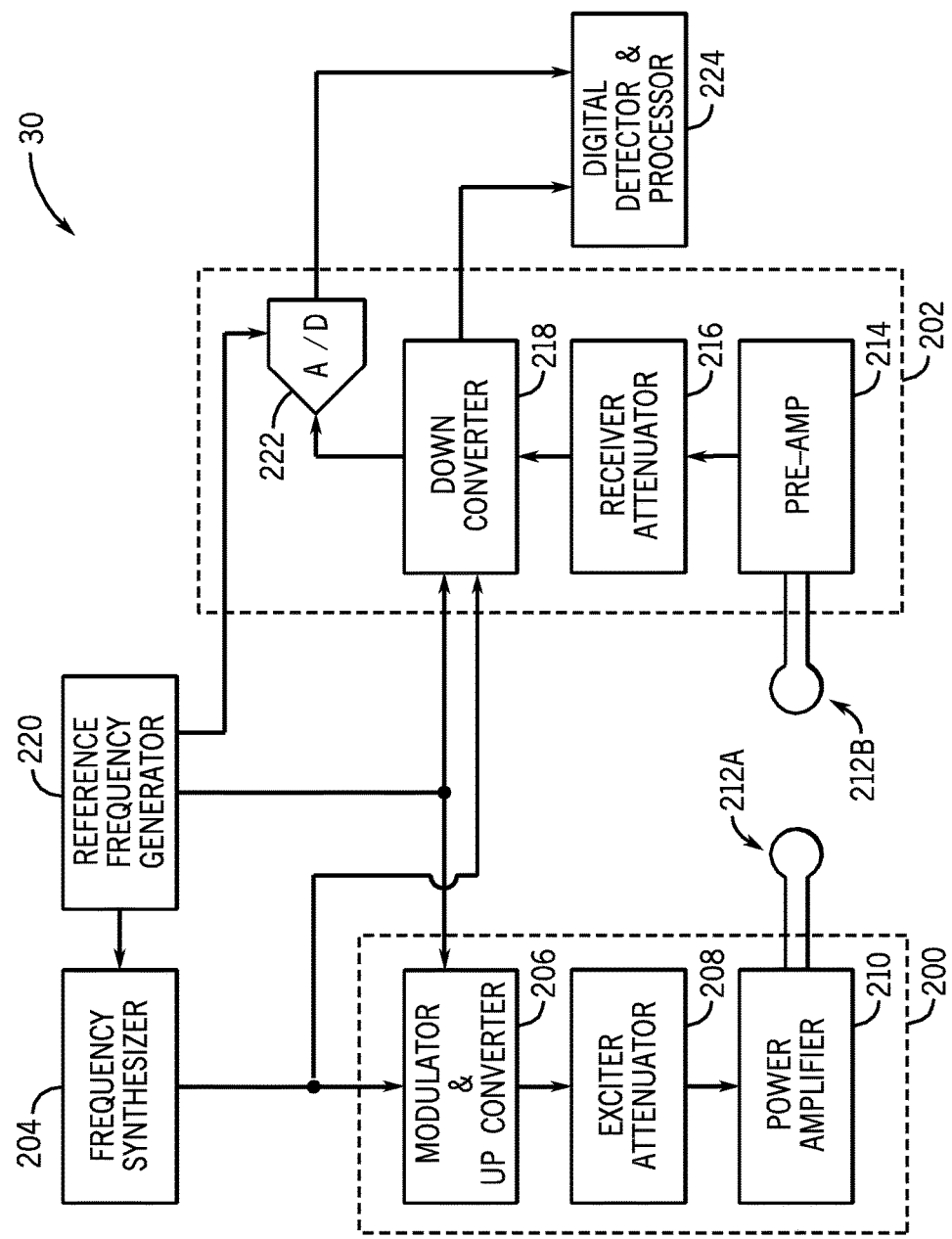
FIG. 2 is a block diagram of an RF system that forms part of the MRI system of FIG. 1.

As shown in FIG. 1, the RF system 30 may be connected to the whole body RF coil 38, or as shown in FIG. 2, a transmitter section of the RF system 30 may connect to one RF coil 212A and its receiver section may connect to a separate RF receive coil 212B. Often, the transmitter section is connected to the whole body RF coil 38 and each receiver section is connected to a separate local coil 212B.

Referring particularly to FIG. 2, the RF system 30 includes a transmitter portion 200 that produces a prescribed RF excitation field and a receiver portion 202 that receives the echo signals from the subject being imaged. Though illustrated as having both transmit 200 and receive 202 stages, it is likewise contemplated that the following components may be further integrated into a common transmit/receive system. Likewise, though a traditional transmit and receive system is described, it is contemplated that transmit and receive systems adapted for parallel imaging or specialized transmit and receive systems further adapted to the present invention may also be utilized.

The base, or carrier, frequency of this RF excitation field is produced under control of a frequency synthesizer 204 that receives a set of digital signals from the pulse sequence server 20 of FIG. 1. These digital signals indicate the amplitude, phase, and frequency of the RF carrier signal produced. The RF carrier is applied to a modulator and up converter 206 where its amplitude is modulated in response to a signal R(t) also received from the pulse sequence server 20 of FIG. 1. The signal R(t) defines the envelope of the RF excitation pulse to be produced and is produced by sequentially reading out a series of stored digital values. These stored digital values may be changed to enable any desired RF pulse envelope to be produced.

The magnitude of the RF excitation pulse produced is attenuated by an exciter attenuator circuit 208 that receives a digital command from the pulse sequence server 20 of FIG. 1. The attenuated RF excitation pulses are applied to a power amplifier 210 that drives an RF coil 212A.

Referring still to FIG. 2 the signal produced by the subject is picked up by a receiver coil 212B and applied to the receiver portion 202 and, specifically, through a preamplifier 214 to an input of a receiver attenuator 216. The receiver attenuator 216 further amplifies the signal by an amount determined by a digital attenuation signal received from the pulse sequence server 20 of FIG. 1. The received signal is at the Larmor frequency, and this high frequency signal is down converted in a two step process by a down converter 218 that first mixes the MR signal with the carrier signal from the frequency synthesizer 204 and then mixes the resulting difference signal with a reference signal from a reference frequency generator 220. The down converted MR signal is applied to the input of an analog-to-digital (A/D) converter 222 that samples and digitizes the analog signal and applies it to a digital detector and signal processor 224 that produces, for example, 16-bit in-phase (I) values and 16-bit quadrature (Q) values corresponding to the received signal. The resulting stream of digitized I and Q values of the received signal are output to the data acquisition server 22 of FIG. 1. The reference signal as well as the sampling signal applied to the A/D converter 222 are produced by the reference frequency generator 220.

Although variations on the above-described MRI systems have been around since approximately 1973, they have traditionally been used strictly for imaging. However, some deviations from "standard" imaging applications have been proposed and, in limited circumstances, used, such as MRI-driven ablation and the like. Recently, it has been proposed to move or deflect nanoparticles formed as or containing ferrous spheres through the vasculature with MRI-based technology. These applications have focused on functions such as drug delivery and have generally been limited to academic settings.

However, the present invention extends the concept of the in vivo manipulation of substances using MRI-based techniques from the nano-level to the macro-level. Particularly, the present invention provides systems and methods for percutaneously adjusting medical implants in patients using the gradient magnetic and RF fields to create desired forces on the medical implants. By coupling systems and methods that exploit the complete control of the field strength (within the gradient bounds) and direction, the present invention enables a high degree of freedom to adjust medical implants by controlling the magnitudes and directions of the applied forces. In addition, by utilizing an MRI system to provide the gradient and RF fields, imaging can be readily integrated with control algorithms to provide imaging of the targeted implant and/or surrounding tissue during adjustment. Therefore, adjustment and control procedures can be monitored with substantially real-time feedback.

As will be described, the present invention provides systems and methods that can be used to control actuators, for example, linear and rotary actuators, in vivo. Specifically, the present invention is particularly advantageous because it is readily compatible with MRI systems that are currently available without substantial modification, for applications both internal and external to patients. The present invention may include actuators that are specifically designed to be powered, for example, solely by the magnetic gradient fields in an MRI machine, such that actuation is non-invasive and requires no external power source connected to the actuator. The actuators can operate in substantially any position and orientation, and actuation and imaging can occur substantially simultaneously to provide control feedback. Multiple actuators can be powered independently or simultaneously, based on the control algorithms.

Specifically, it is a common understanding that ferromagnetic materials of any substantial size, such as larger than a nanoparticle, cannot be placed safely into the bore of an MRI machine. This is such a strong belief that MRI compatible actuator design guidelines, written in multiple technical papers, state that only non-ferromagnetic materials must be used in actuator designs for use within an MRI bore.

Figure 3:
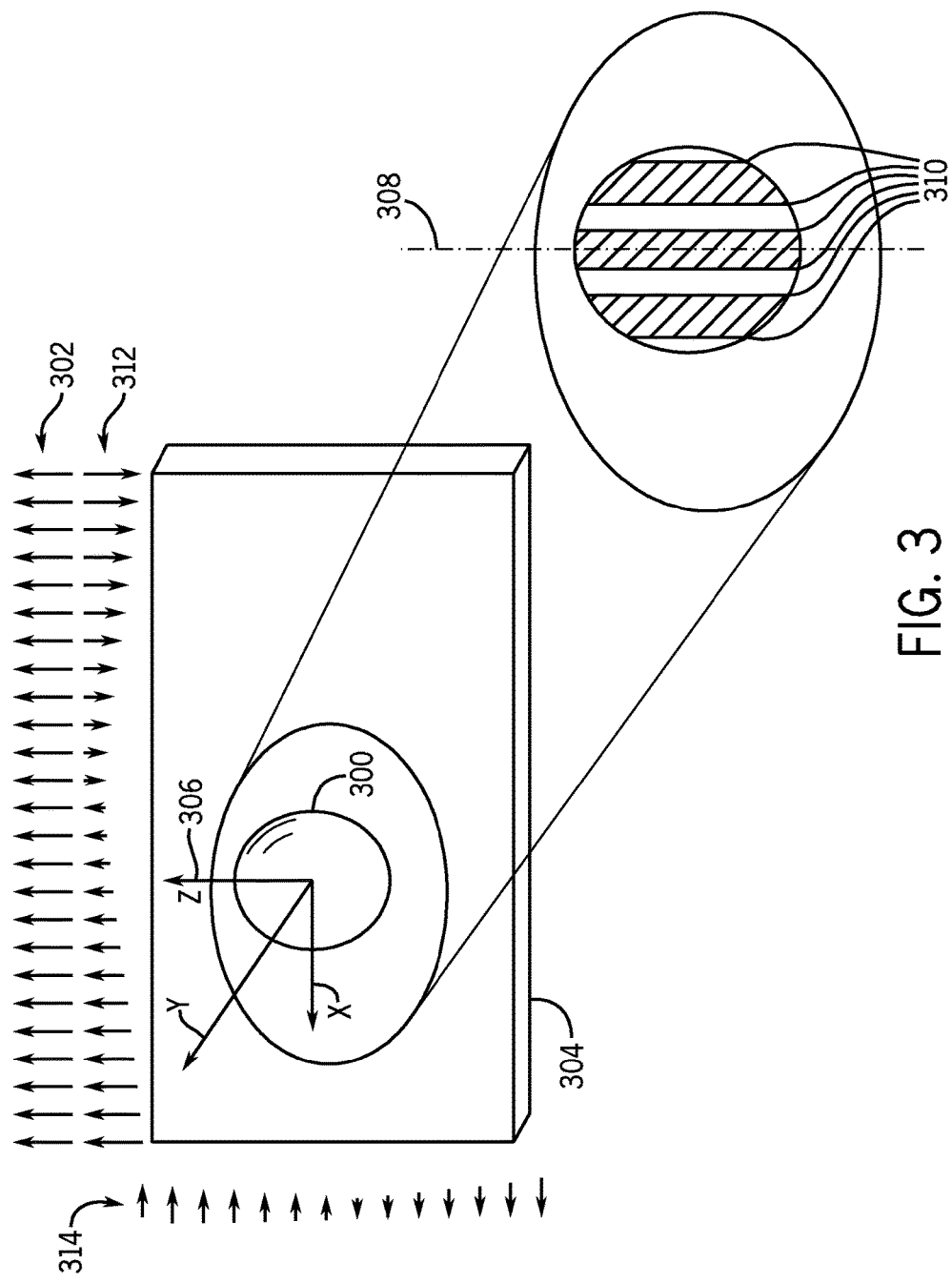
FIG. 3 is a perspective view of a ferromagnetic or ferrimagnetic sphere arranged in a bore of the MRI system of FIG. 1 and illustrating the challenges with direct control of a medical device through an affixed ferromagnetic or ferrimagnetic object using magnetic fields such as available in the MRI system of FIG. 1.

Specifically, referring to FIG. 3, a perspective view is provided showing a macroscopic ferromagnetic or ferrimagnetic material 300 and a static magnetic field 302, for example, such as is available in traditional MRI systems. For purposes of brevity the macroscopic material will be referred to hereafter as a ferromagnetic material, but it is recognized that it could be a ferromagnetic or ferrimagnetic material (that is, any material arranged to develop or possess sufficient magnetization to perform as described). The macroscopic ferromagnetic material 300 is arranged on a plane 304, such as a table of an MRI system. For purposes of discussion, the static magnetic field 302 will be described as being that of an MRI system such as described above, but could be of other systems for generating the desired magnetic fields. With the macroscopic ferromagnetic material 300 arranged in the static magnetic field 302, the interactions therebetween depend on size, shape, and magnetization properties of the macroscopic ferromagnetic material 300 and, as will be described, the application of additional magnetic fields, such as gradient fields and/or shaped fields, such as a $B_1$ field of traditional MRI systems. In general, every ferromagnetic material 300 placed in a strong, static magnetic field 302, such as the $B_0$ field of an MRI system, will reach a high magnetization, most often its saturation magnetization, forming an internal magnetization vector 306 (if saturated, magnitude of saturation) aligned with the static, magnetic field 302.

The torque aligning the magnetization vector 306 with the static, central magnetic field 302 and hence maintaining alignment of the magnetization vector 306 with the static magnetic field 302 is proportional to the magnitude of the central magnetic field 302 and the volume of the material 300, as given by:

$$\text{Torque} = \text{Volume} * (\text{Magnetization}) * (\text{Magnetic Field Strength});\quad\text{Eqn. 3.}$$

This torque is significant in magnitude, typically by orders of magnitude higher, compared to any other torque discussed in the following description, and hence the magnetization vector 306 is generally assumed to maintain alignment with the static field.

As will be described, the present invention recognizes that the formation of the magnetization vector 306 in response to the static magnetic field 302 favors the direction of spontaneous magnetization internal to the material, and therefore, it favors an easy axis 308 of the macroscopic ferromagnetic material 300. The easy axis (multiple easy axes may exist) depends on anisotropy in the material: crystal, shape, stress, induced (magnetic annealing, plastic deformation, and irradiation), and exchange anisotropy, and considering all applicable anisotropies, the easy axis is the axis of minimum total energy. If no magnetic anisotropy exists, then the magnetization vector 306 does not have a favored axis 308. However, most common materials, especially with the body-centered cubic crystal structure in iron, have a significant degree of magnetic anisotropy and hence at least one easy axis 308. An applied, external torque must do work against the anisotropy force to form a magnetization vector 306 off of the easy axis 308. Therefore, if an easy axis 308 does not align with the static magnetic field 302 due to an external torque, anisotropy energy is stored in the material 300 that causes the material 300 to continue to favor alignment along its easy axis 308 (or one of its easy axes, if more than one) with an internal, reaction torque (if more than one easy axis, the favored axis may change as the external torque varies). If the external torque is removed, the favored easy axis 308 would then return to alignment with the static magnetic field 302, and hence the magnetization vector 306.

Thus, once an unconstrained macroscopic ferromagnetic material 300 is placed into the bore of an MRI system, grain growth occurs for the domains 310 that are aligned favorably with the applied field. Unfavorably aligned domains decrease in size and eventually can overcome their anisotropy energy and rotate from their original direction of magnetization, ultimately to the direction of the bulk material easy axis of magnetization, due to the applied high field energy. Once complete alignment with the applied field occurs and the material is magnetically saturated, then the bulk material behaves as a single-domain sample. In any case, in the high static field in the MRI bore, the bulk easy axis 308 will almost immediately align with the central, $B_0$, field 302 and will maintain alignment due to forceful torques, as dictated above. These torques, based on magnetization vector 306 alignment with both the central, static field 302 and with an easy axis 308, generate many of the limitations for placing macroscopic ferromagnetic materials into the bore of an MRI system, because the sudden torque on any improperly constrained macroscopic ferromagnetic material 300 could cause and has, unfortunately, caused serious injury to the subject. For example, it is general practice that bone screws (typically with high levels of anisotropy) are not placed in the bore of an MRI system until the screws are set and the bone is completely hardened and, even then, it is recommended to be avoided.

Once the magnetization vector 306 is formed, controllable forces can be applied to the ferromagnetic material using the gradient fields along all three axes in the MRI bore, as given by:

$$\text{Force} = \text{Volume} * (\text{Magnetization}) * (\text{Gradient Field Strength});  \quad \text{Eqn. 4.}$$

As will be described, since gradient fields of an MRI system are independently controllable along all three axes, controlled, three dimensional movement of an unconstrained sphere should be possible. However, the anisotropy of the material 300 must first be considered. In order to control the potential for complications caused by the sudden torque exerted by a macroscopic ferromagnetic material 300 aligning with the static, $B_0$, field 302 of an MRI system, the present invention may employ a spherical shape. Since a sphere is perfectly symmetric, it eliminates shape anisotropy, which typically has a strong associated torque.

To further complicate matters, despite the use of a spherical geometry to reduce the potential for undesirable, geometric torsion effects of sudden and/or uncontrolled influences on a macroscopic ferromagnetic implant on a subject arranged in an MRI system, generally, macroscopic ferromagnetic materials are not or cannot be effectively and efficiently created to be perfectly isotropic, in relation to the additional forms of anisotropy. Therefore, a favored easy axis 308 still exists. Macroscopic materials, such as the described macroscopic sphere 300 are not, typically, perfectly homogeneous. The macroscopic components typically include "grain boundaries" or other variances in the magnetic susceptibility or magnetic properties of adjacent portions 310 of, for example, the above-described macroscopic ferromagnetic material 300, which typically prevent magnetic isotropy of the material. As described above, in many cases, for example, macroscopic components made of iron, the macroscopic components may have a significant degree of magnetic anisotropy and hence at least one easy axis. Accordingly, despite the fact that the macroscopic ferromagnetic material 300 has a spherical shape, the macroscopic ferromagnetic material 300 may not move the same in all directions with applied magnetic fields.

That is, despite, for example, the fact that the macroscopic ferromagnetic material 300 has a spherical shape and should roll in the labeled "z-direction" in response to a magnetic field gradient 314 applied along the z-direction, the macroscopic ferromagnetic material 300 may slide or be otherwise "pushed" because the internal torque induced by anisotropy maintains the alignment of the magnetization vector 306 with the material easy axis 308, which then maintains its orientation with the static field 302, based on Equation 3 (noting that due to the relatively small size of the gradient fields, the effects of gradient fields on the orientation of the magnetization vector 306 can be substantially ignored for purposes of this explanation). It is only likely that the sphere will roll in the "z-direction" under the circumstance that the friction between the sphere and the surface it sits on is high enough to prevent sliding and the linear applied force to the sphere is large enough to generate a torque to overcome the anisotropy torque of the material. For these reasons, the above-described macroscopic ferromagnetic material 300 interferes with the ability to roll. However, to add further complexity to the ability to manipulate the macroscopic ferromagnetic material 300, in the illustrated example, the macroscopic ferromagnetic material 300 may roll when subjected to a magnetic field gradient 312 applied along the "x-direction" due to the orientation of the magnetization vector.

Figure 4:
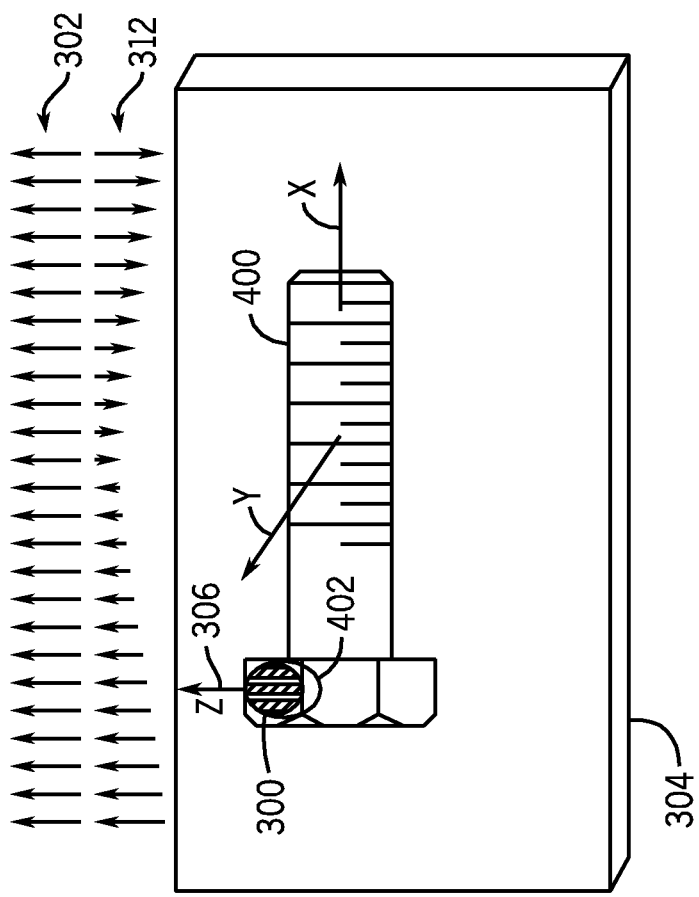
FIG. 4 is a perspective view of a medical device having a cavity with a ferromagnetic or ferrimagnetic sphere arranged therein for indirect manipulation of the medical device using magnetic fields such as available in the MRI system of FIG. 1.

Referring now to FIG. 4 to further overcome these complications, the present invention imbeds the ferromagnetic material 300 in a non-ferromagnetic material 400, and then manipulates the ferromagnetic material 300, in order to achieve desired motions of the object as a whole. In some cases, though, the non-ferromagnetic material 400 may, in fact, incorporate a ferromagnetic material, but one that has lower magnetization than the ferromagnetic material 300. In that case, the material having lower magnetization may create competing forces and torques to those generated in the ferromagnetic material 300, but at a sufficiently low magnitude that the ferromagnetic material 300 would still be controllable, as described herein. In the illustrated example provided in FIG. 4, the ferromagnetic material 300 is formed as a sphere that is disposed within a cavity 402 arranged in the non-ferromagnetic material 400, which is illustrated as being in the form of an implantable bolt. Though a bolt is illustrated, as will be further detailed, it is contemplated that the non-ferromagnetic material 400 form a component of a wide variety of implantable devices, including devices composed of multiple components in an assembly for example, including artificial valves, an annuloplasty ring associated with a heart implant, an artificial chord associated with a heart implant, pediatric implants, orthopedic implants, and many other implants.

In particular, since the devices have at least one component which is also a self-contained actuator and the magnetic fields travel through tissue essentially undisturbed, they can be placed and actuated both internal and external to the body. Therefore, an adjustable implant, for example, can be implanted into a patient, and then continuously adjusted for the lifetime of that patient without any additional invasive procedures. Cardiac implant applications used to repair the mitral valve can readily benefit from the present invention. However, additional examples of commonly adjusted implants that would benefit include spinal screws for scoliosis, laparoscopic adjustable gastric bands for obesity, and pediatric implants to account for growth.

By arranging the ferromagnetic materials 300 as spheres disposed in the cavities 402, the spheres are free to rotate. These "free-to-rotate" spheres provide a number of substantial advantages. For example, the magnetization vectors 306 can align with their easy axes 308 during the entry of the overall device within the magnetic fields 302, 312, and 314 (or any other magnetic fields that exist), and the torque produced by anisotropy does not need to be overcome with the applied forces. That is, by arranging the ferromagnetic sphere inside the cavity, the sphere is free to move and rotate within the cavity. Thus, with respect to the forces applied to the non-ferromagnetic implant, the particular motion (e.g., rotational vs. sliding, etc.) of the ferromagnetic sphere within the cavity is irrelevant because the resulting force applied to effectuate manipulation of the non-ferromagnetic implant is substantially similar irrespective of particular motion (e.g., rotational vs. sliding, etc.) of the sphere within the cavity. For purposes of discussion, this concept can be referred to as "indirect" manipulation of the non-ferromagnetic implant through the free-to-move/rotate, ferromagnetic sphere. With respect to small scales, cavities (of all scales and not necessarily spherical cavities) may be injected with a ferrous micro-fluid or nano-fluid, in order to provide at least low friction translation or rotation of its micro-spheres or nano-spheres, respectively, which then induces the desired forces of motion to the non-ferromagnetic implant.

Pure linear motion of a sphere can be used, for example, to drive a linear ratchet mechanism constructed from non-ferromagnetic material(s) 400. However, the application of linear forces on the spheres can also create rotary motion, based on proper constraints and controlled forces. Rotary and linear motion combinations are also possible.

Though more complex than linear motion, controlled rotary motion is readily achievable by rotating a configuration such as illustrated in FIG. 4. For example, a free-to-rotate, chrome steel sphere can be embedded into a slightly larger diameter (to reduce friction) cavity in a plastic cylindrical bolt. By applying a rotating gradient field, linear forces (continuously changing direction in rotation) can be applied to the sphere to rotate the bolt to translate along the "x-direction". Such control can be achieved for forward and backward motion along any axis in three dimensional space.

While FIG. 4 illustrates a configuration utilizing only one sphere, multiple spheres can be used to increase the magnitude of the applied force. Spreading the effective volume over multiple spheres provides further design freedom in the actuator geometry. The effects of the sphere on the static field fall off with the inverse of its radius to the third power, and the effects of the sphere on the gradient field fall off with the inverse of its radius to the fourth power. Therefore, the magnetic effects of two adjacent spheres on each other is proportional to the inverse of their radius to the third and fourth powers. Therefore, although some applications device design calls for adjacent spheres to not directly contact each other, depending on device design and application, the spacing to maximize the effective actuation volume does not often pose a large geometric constraint. If the spheres were able to move about and contact one another, the spheres may align in a row with the magnetic field (contacting each other) and behave like a bar magnet. If independent cavities, each containing a sphere, are present, actuation is dependent on achieving at least a minimum spacing of the spheres in separate cavities in the scaffold. If the spheres are too close, actuation may not be possible, as the magnetic fields of the spheres interact/interfere with each other at a magnitude that may approach (or possibly even exceed) and interfere with the magnitude of the applied gradients. This spacing depends on sphere volume, magnetization, and field strengths. Shielding may be applied to reduce this distance; however, the shielding must not shield the applied gradients with respect to all the spheres used for actuation, and to be feasible for actuation, may lead to complex sphere arrangements.

Though the above-described invention for the non-invasive, in vivo manipulation of medical implants can be used with a variety of systems capable of providing the adjustable magnetic fields used to manipulate the ferromagnetic materials arranged in the medical implants, MRI systems provide a variety of advantages. First, MRI systems inherently include the systems to create and control, with a high degree of accuracy, the adjustable magnetic fields used to manipulate the implant. Also, MRI systems are readily available and widely used in clinical settings. In addition, MRI systems are highly programmable. Finally, by their nature, MRI systems are designed to perform imaging procedures of subjects arranged within the bore of the system. Accordingly, when using an MRI system to achieve and control the magnetic fields designed to manipulate a medical implant in accordance with the present invention, imaging procedures can be advantageously coupled with and performed during the process of manipulating the medical implant using the MRI system.

Figure 5:
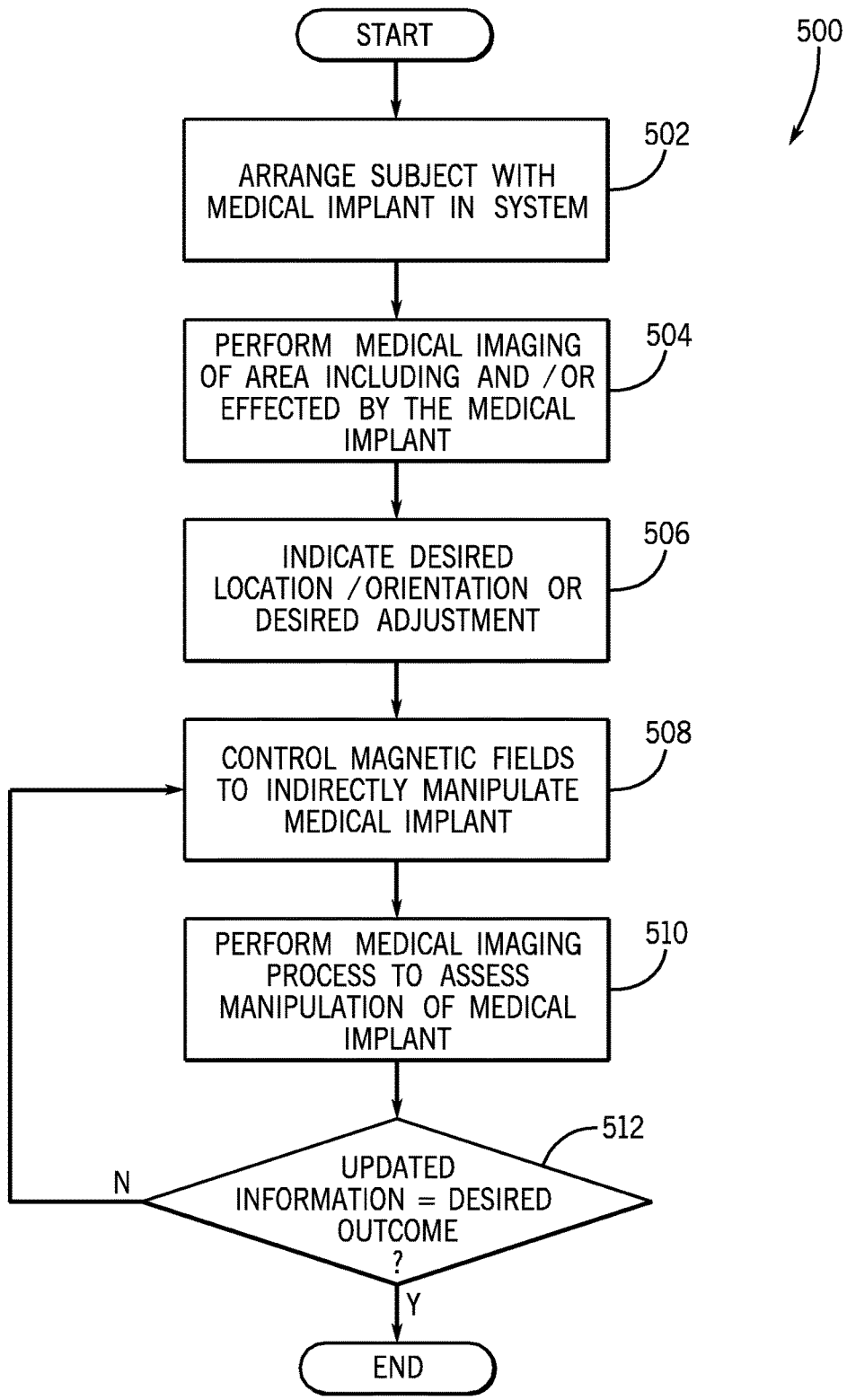
FIG. 5 is a flow chart setting forth the steps for a method to be performed using the systems of FIG. 1 in accordance with the present invention.

In particular, referring to FIG. 5, a flow chart is provided setting forth the step of a method 500 in accordance with the present invention. The method begins at process block 502 by arranging a subject having a medical implant arranged therein within a system capable of effectuating the desired adjustable magnetic fields described above, such as an MRI system. As described above, the device includes at least one cavity within which a ferromagnetic material, preferably a macroscopic ferromagnetic sphere is arranged. Thereafter, at process block 504, a medical imaging process is performed to acquire data from an initial location including the medical implant and/or tissue effected by its adjustment and/or identification markers and, in some instances, the specific location and/or orientation of the medical device and/or macroscopic, ferromagnetic sphere arranged within the medical implant. Specifically, in some cases, the imaging may include imaging the medical implant itself. However, it is not always necessary to image the implant itself. In some cases it may be suitable to image the specific geometry of tissue and/or physiological conditions. At process block 506, the clinician indicates a desired location and/or orientation of the medical implant relative to an initial location and/or orientation or a desired adjustment to reach new tissue geometries and/or physiological conditions. While in many cases, this may be achieved by imaging the medical device directly or indirectly, this step can be done without ever imaging the device itself. For example, in certain cases, such as cardiac applications, the adjustments to reach a specific physiological condition detected by the physiological acquisition controller 40 of FIG. 1 is a very compelling benefit that does not necessarily require direct or indirect imaging of the medical implant.

At process block 508, the system is used to create and control magnetic fields specifically designed to indirectly manipulate the non-ferromagnetic medical implant by manipulating the macroscopic, ferromagnetic sphere arranged in the cavity within the medical implant. This may be done, for example with computer aid by providing, for example, the above-described computer system of an MRI system with the desired location and/or orientation information from process block 506 to thereby tailor a gradient and/or RF pulse sequence designed to adjust the location and/or orientation of the medical implant from the initial location and/or orientation to the desired location and/or orientation provided at process block 506.

Thereafter, at process block 510, another medical imaging process may be performed following the manipulation performed at process block 508. Again, this imaging process could be to directly or indirectly image the manipulation of the medical device or to assess an effect of the adjustment to the tissue and/or the physiological effect(s) of any manipulation. Using the information acquired at process block 510, a check is made to determine whether the updated information acquired at process block 510 following the manipulation performed at process block 508 matches a desired outcome, such as may be indicated at process block 506. If not, the control and imaging processes of process blocks 508 and 510 are repeated until the desired outcome is determined to have been achieved. The desired outcome in 506 maybe updated during the procedure, for which would drive the subsequent processes in 508, 510, and 512.

In an alternative implementation, a machine can be constructed that is configured to be manipulated by a magnetic resonance system capable of effectuating the desired adjustable magnetic fields, as described above. The machine can incorporate non-ferrous scaffolds and/or non-ferrous constraining systems. One or more ferrous structures, such as ferrous spheres, positioned within cavities formed in the scaffolding can then be manipulated by the adjustable magnetic fields to effect a particular operation of the machine.

To provide multiple operations, the machine may include a number of separate ferrous actuators (independent or dependent) that are each actuated by the application of a magnetic field along a particular axis, about a particular plane, or along a particular path. In one implementation, each axis, plane, and/or path can be arranged to be substantially orthogonal during actuation to one another such that the application of an actuating magnetic field to one of the ferrous actuators does not affect (or only temporarily affects) the remaining ferrous actuator functions. In this manner, the machine may provide a number of separate functions that can each be separately controlled. In other implementations, though, the machines may incorporate a number of locks or brakes that can be separately actuated in order to provide the machine with additional control of degrees of freedom to provide desired features or functionality.

One example machine includes a robotic biopsy machine or device. Generally, a robotic biopsy device is configured to provide a number of functions including: 1) orienting the biopsy needle towards the region of interest, 2) inserting the biopsy needle into the region of interest (in one implementation a maximum biopsy puncture force exceeding 4 N can be a functional requirement of such a biopsy device, which depends on the tissue properties along the biopsy path and region of interest), 3) taking a biopsy sample by actuating the needle, and 4) removing the needle and enclosed tissue sample from the patient.

In order to operate such a biopsy device to be correctly positioned in one functional application plan, the biopsy device's needle must be able to translate the surface of the skin (e.g., through the MRI's x/z plane) and rotate about a point (e.g., rotate about the MRI's x- and z-axes). As such, the biopsy device may require at least four degrees of freedom (DOFs) to achieve the desired, fine-tuned needle position. Once the needle has been positioned or oriented correctly, the needle must be actuated to perform the biopsy. That needle actuation (e.g., the application of a puncture force by the needle) requires that the biopsy device have an additional DOF along the length of the needle in order to introduce the needle into the desired tissue and then withdraw the needle from that tissue. As such, the specified biopsy device requires 5 DOFs to allow for accurate positioning of the biopsy needle, as well as actuation of the needle to perform the biopsy.

In many machines, independent DOFs are achieved using separately-controllable actuators. The present biopsy device, however, incorporates an actuator design that allows a single actuator (e.g., a single ferrous sphere) to achieve multiple, independent actuation modes. Each mode of that single actuator can operate as an independent actuator by moving within independent axes, planes, or paths or by disabling all other modes during actuation. In such a configuration, combinations of modes (dependent and independent) are also possible. In one design, a single ferrous sphere or other object can actuate every degree of freedom of the machine. Additionally, individual degrees of freedom of the machine can be turned "off" and "on" using different braking mechanisms incorporated into the machine. These breaking mechanisms are activated using the MRI gradient fields. Because the braking mechanisms include ferrous materials, they can be designed to add additional actuation volume to specific modes of actuation.

Figure 6:
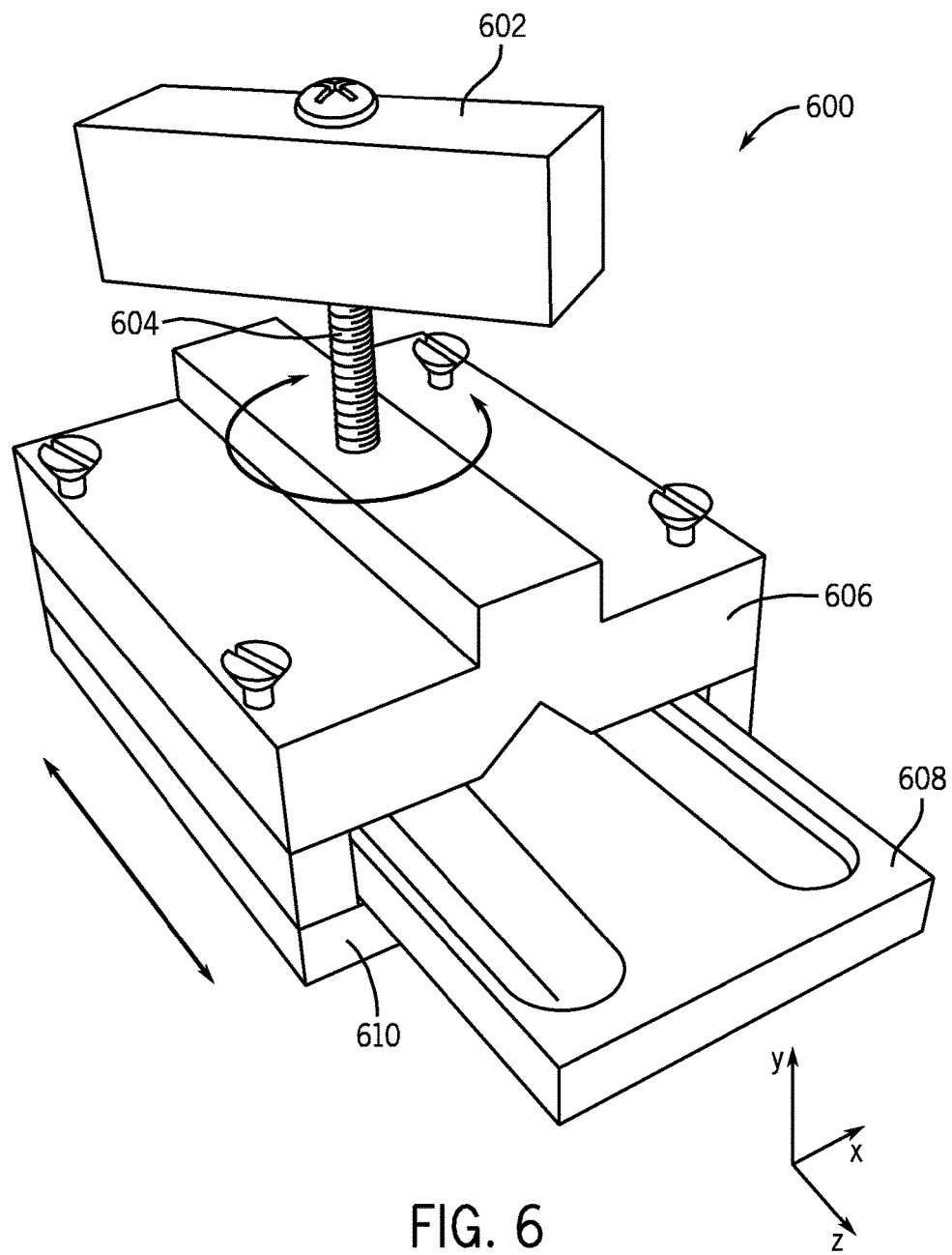
FIG. 6 is an illustration of a device having two degrees of freedom (DOF) that may be operated by an MRI gradient field to perform various functions, such as a biopsy.

FIG. 6, for example, is an illustration of a machine having two DOFs that may be operated by an MRI gradient field to perform various functions, such as a biopsy. Generally, the machine is constructed from MRI-compatible (e.g., non-ferrous) materials, but include a number of ferrous objects (in one implementation, spheres) that allow for manipulation of the machine by the application of an appropriate magnetic gradient. Machine 600 includes a rotatable component 602 configured to rotate about threaded shaft 604. Component 602 includes a ferrous object (e.g., sphere) positioned away from the axis of threaded shaft 604. As such, by application of a specific rotational gradient field, component 602 will rotate causing shaft 604 to also rotate. Shaft 604 is threaded and connects with a threaded nut formed within body 606 of machine 600. Accordingly, as rotatable component 602 rotates, shaft 604 moves either into, or out of, body 606. This axial movement of shaft 604 may be used in a biopsy machine, for example, to move a needle into target tissue in order to perform a biopsy, where the needle extends out of the bottom surface of bodies 606, 608, and 610.

In this design and for its intended biopsy application, no braking mechanism is required to stop undesired rotation of component 602 because a very specific, rotational gradient field is required for functional actuation and imaging gradients are not large enough to generate motion due to friction in the system.

Machine 600 also provides a second DOF by allowing body (or carriage) 606 to be slid forwards or backwards on linear guide rail 608 of machine 600. To actuate this second DOF, the ferrous object (e.g., sphere) in 602 is used, along with a ferrous object (e.g., sphere) that is disposed within a space contained by body 610. A linear magnetic gradient can then be applied to those ferrous objects causing body 606 and the body 610 to which it is fixed, to move either forwards or backwards on linear guide rail 608. When rotational component 602 and shaft 604 are mounted directly to body 606, as in this case, this movement of body 606 allows the position of shaft 602 (and any medical device, such as needle, connected thereto) to be adjusted.

In one implementation, body 610 of machine 600 is a brake housing. Brake housing 610 includes a brake system (illustrated in FIGS. 7A, 7B, and 7C) that can be selectively employed to limit movement of body 606 on linear guide rail 608. By positioning the brake in its locked position, when applying the rotational gradient field to cause movement of rotational component 602, unwanted movement of body 606 on linear guide rail 608 can be avoided at times during which the rotational gradient field is orientated so as to cause movement of body 606 on linear guide rail 608.

FIGS. 7A, 7B, and 7C are illustrations showing the internal components of brake housing 610 that may be incorporated into machine 600 to control a movement of body 606 on linear guide rail 608. Each of FIGS. 7A, 7B, and 7C show a top view of brake housing 610. Housing 610 includes groove 702 with two springs 704a and 704b being mounted at opposite ends of groove 702. Springs 704 include an MRI-compatible, or non-ferrous, material such as beryllium copper. Both springs 704a and 704b are connected to wedges or chocks 706a and 706b, respectively. Springs 704 operate to bias wedges 706 towards a center of brake housing 610. Wedges 706 each have a sloped face surface 708 oriented so that the lower portions of the face surface 708 are closer to one another than the upper portions of each face surface 708 and a flat face surface 709. To prime the braking system, a ferrous object (e.g., a sphere) 710 is positioned between the flat face surfaces 709 of wedges 706.

The dimensions of springs 704, wedges 706, and sphere 710 are selected so that, when the brake system is primed, springs 704 cause the flat face surfaces 709 of wedges 706 to press against sphere 710 holding the sphere in a lowered position (see FIG. 7B). To, trip the brake, a magnetic gradient is applied to sphere 710 in the positive Y-axis direction (see the axis in FIG. 7C). This moves sphere 710 upwards away from flat face surface 709 until sphere 710 is positioned between the sloped face surfaces 708 of wedges 706. With sphere 710 positioned between the sloped face surfaces, the compressive force of springs 704 applied to wedges 706 translates into a vertical force pushing sphere 710 into a upwards position, as shown in FIG. 7C. This causes the sphere to be raised upwards at least partially out of brake housing 610. In this condition, sphere 710 is biased in the raised position by springs 704.

Depending upon the strength of springs 704, slope angle of face 708, friction coefficient of faces 708 and 709, and the maximum possible gradient field, it may be possible to reset the brake. To reset the brake, sphere 710 is lowered from this raised position by applying a linear gradient downwards along the Y-axis to pull sphere 710 downwards into a lowered position within brake housing 610. This lowered position is shown in FIG. 7C. If the applied gradient is sufficiently strong, the downward force applied to sphere 710 presses against the sloped faces of wedges 706. The force applied to the faces of wedges 706 is then translated into a compressive force applied to each of springs 704. As the springs compress, the wedges 706 withdraw away from sphere 710 allowing the sphere to drop into a withdrawn position within brake housing 610 between the flat face surfaces 709 of wedges 706. To facilitate movement of wedges 706 through groove 702, PTFE or Teflon inserts, or inserts coated or made of another low-friction material, may be positioned underneath wedges 706 (or on any contact surfaces) or over any of the faces of wedges 706 to minimize system friction. To facilitate movement of the sphere when it is between the flat faces 709 or sloped faces 708, the faces of the wedges 706 or the surfaces that they contact may be made of or coated with a low-friction material, such as Teflon. Instead of inserts, the current surfaces may also be coated with a low-friction material.

This movement of sphere 710 within brake housing 610 can thus be used to provide a braking mechanism for machine 600 to control the movement of body 606 across the linear guide rail 608.

As shown in FIG. 6, brake housing 610 is positioned below linear guide rail 608 and in fixed connection with body 606 to from a carriage. Brake housing 610 is positioned so that when the brake is applied sphere 710 is biased in its upwards position against a lower surface of linear guide rail 608 by the compressive force of springs 704. FIG. 8A is a side view of linear guide rail 608 and brake housing 610 showing the sphere of brake housing 710 pressing against a lower surface of linear guide rail 608. With sphere 710 pressing against the lower surface of linear guide rail 608 with the necessary force, movement of the carriage consisting of bodies 606 and 610 is inhibited. The necessary force is dependent on the forces of motion that the brake is inhibiting and the coefficient of friction of the surface of linear guide rail 608 that the sphere is pressing against. Additionally, it should be obvious to a person skilled in the art that the linear guide rail does not necessarily need to be linear or planar.

In some cases, the portion of the lower surface of guide rail 608 that contacts sphere 710 when sphere 710 is in the raised position may incorporate a surface coating or treatment to increase the friction between the lower surface of guide rail 608 and sphere 710 improving the resistance of motion between guide rail 608 and brake housing 610 to further inhibit movement of the carriage consisting of fixed bodies 606 and 610. In one specific implementation, a groove is formed in the lower surface of guide rail 608. The groove incorporates a friction-increasing surface treatment and is sized to receive sphere 710. By incorporating a groove sized to receive sphere 710 into the lower surface of guide rail 608, the amount of resistance force to motion between guide rail 608 and sphere 710 when sphere 710 is in the upwards, or locked position (see, for example, FIG. 8A) is increased, further improving a stable, static connection between guide rail 608 and sphere 710 to enhance the braking affect of sphere 710. In the current design, the purpose for the groove in the guide rail is also to fully constrain the sphere from linear motion in its locked position.

To release the brake and allow movement of carriage body 606 with respect to guide rail 608, a sufficiently strong gradient field may be applied to sphere 710 along the negative Y-axis (e.g., in a downwards direction). If the gradient is of sufficient magnitude, sphere 710 is pulled downwards away from the lower surface of guide rail 608, thereby unlocking carriage body 606. FIG. 8B illustrates sphere 710 in this downwards, or unlocked position. With sphere 710 withdrawn from the lower surface of guide rail 608, carriage body 606 fixed to braking mechanism 610 is free to move within along the guide rail 608. Because the movement of carriage body 606 is initiated by the application of a gradient in the horizontal plane (i.e., the plane formed by the X and Z-axis) in the current design, the gradients used to engage or disengage the braking mechanism (i.e., control the movement of sphere 710) are orthogonal to the gradient used to move carriage body 606 and will not interfere with one another.

In more general implementations, therefore, assuming that brake housing 610 is controlled by the application of a magnetic gradient field along the Y-axis, brake-housing 610 can be used to inhibit movement of an object in the X-Z plane. To use brake housing 610 in such a manner, the brake housing must only be positioned sufficiently close to the object that it is supposed to be pressed against, so that when the housing is locked, sphere 710 is put into contact with the object, and when the housing is unlocked, sphere 710 is withdrawn from, and not touching, the object. Accordingly, brake housing 610 can be incorporated into many mechanisms, machines, or devices that require a mechanism to selectively prevent movement of a component by the application of an appropriate magnetic gradient. In some implementations, a magnetic field may be applied to the brake to only partially withdraw the ferrous object into the brake housing. In that case, the brake may only act to apply a friction force that inhibits movement of the object, while still allowing some movement.

Figure 11:
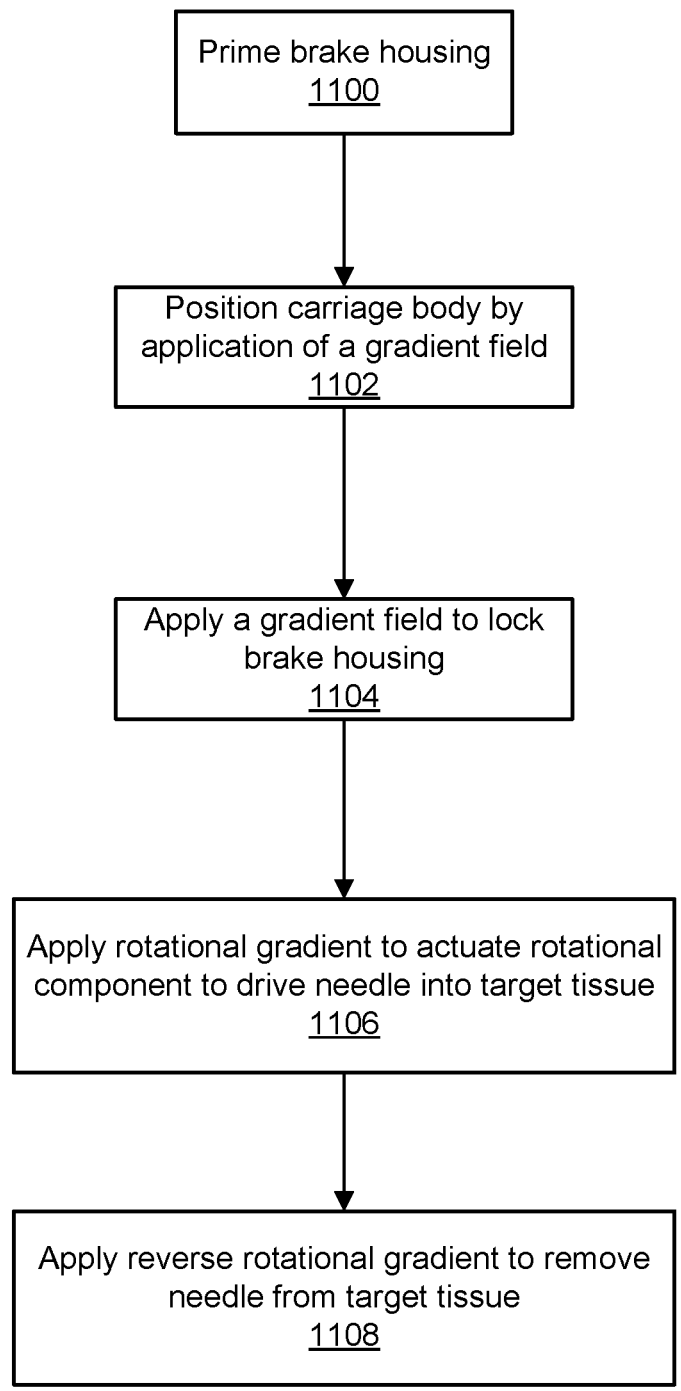
FIG. 11 is a flowchart illustrating an example method of operating the device shown in FIG. 6.

Returning to FIG. 6, therefore, an example use of the machine 600 in a biopsy implementation may involve the following steps, as illustrated in FIG. 11. First, in step 1100 brake housing 610, and sphere 710 are primed in their unlocked position with sphere 710 being positioned between flat face surfaces 709 of wedges 706. Sphere 710 is held in that unlocked position by the compressive force of springs 704. With brake housing 710 in its unlocked condition, carriage body 606 (and the connected rotational component 602) is positioned at the desired location by the application of a gradient field along the X-Z plane in step 1102. With carriage body 606 correctly positioned, for example, a needle connected to rotational component 602 is positioned over tissue from which the biopsy is to be retrieved.

In step 1104, with carriage body 606 and rotational component 602 correctly positioned, a gradient is applied in the positive Y-axis direction to lock brake housing 610 by pulling sphere 710 upwards until it is positioned between the sloped faces 708 of wedges 706 and, as a result, is biased in its upwards positioned, thereby locking brake housing 610, and hence the carriage body 606 and rotational component 602 to which it is fixed.

In step 1106, with carriage body 606 locked, the rotational component 602 can be actuated using a rotational magnetic field to move threaded shaft 604 through body 606. This axial movement of shaft 604 can be used to drive the puncture force of a needle connected to rotational component 602 to begin the biopsy process in the desired tissue. The connection constraint of the needle can be such that the needle rotates with rotational component 602, or such that the rotation and translation of rotational component 602 moves the needle linearly downwards and upwards without rotation.

After introducing the needle, in step 1108 the rotational component 602 is again actuated using another rotational magnetic field to withdraw the connected needle (by rotating the rotational component 602 in the opposite direction and thereby withdrawing shaft 604 from body 606 in the positive y-direction) from the tissue to complete the biopsy.

Figure 9:
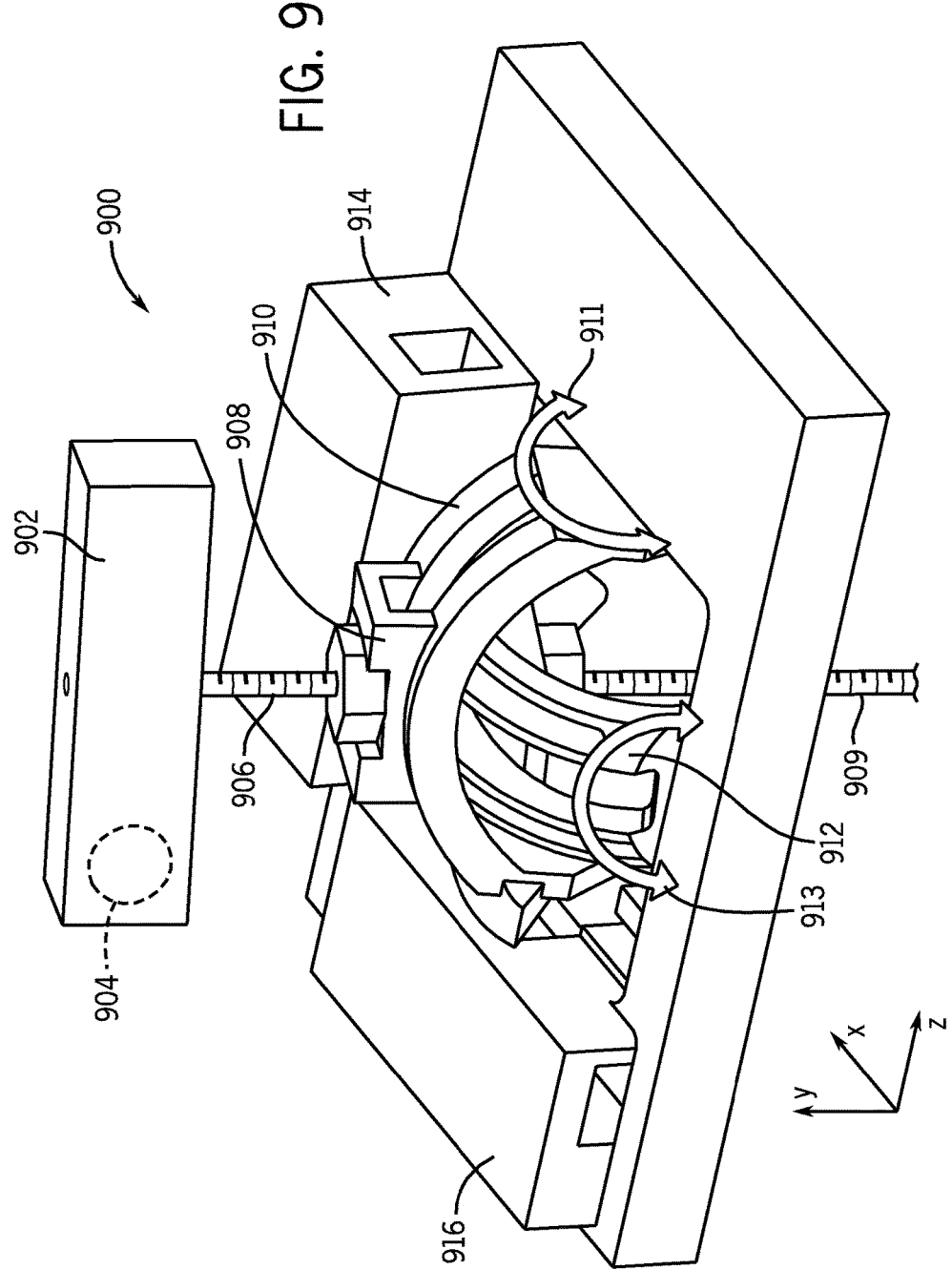
FIG. 9 is a perspective view of a biopsy device configured to allow for accurate orientation of a biopsy needle with respect to a target tissue, and then actuation of the needle to apply a puncture force in order to take a sample from that tissue.

FIG. 9 is a perspective view of a biopsy device 900 configured to allow for accurate orientation of a biopsy needle with respect to a target tissue, and then actuating the needle to apply a puncture force in order to take a sample from that tissue. Generally, the machine is constructed from MRI-compatible (e.g., non-ferrous) materials, but include a number of ferrous objects (in one implementation, spheres) that allow for manipulation(s) of the machine by the application of an appropriate magnetic gradient(s). In one implementation, to provide additional functionality to device 900, the components of the device may be mounted to a guide rail (e.g., such as guide rail 608 shown in FIG. 6) to provide an additional DOF and allow for translation of several of the components of device 900 along a horizontal plane.

Device 900 includes torque arm 902 connected to threaded shaft 906. Torque arm 902 includes a ferrous material (e.g., sphere) 904 positioned away from the axis of threaded shaft 906. As such, by application of a specific rotational gradient field, torque arm 902 will rotate causing shaft 906 to rotate in the same direction. Shaft 906 is coupled to a threaded connection (e.g., a nut) formed within or connected to needle guide 908. Accordingly, as shaft 906 rotates, shaft 906 will either screw into (e.g., through), or out of needle guide 908 resulting in axial movement of shaft 906. Shaft 906 is connected to biopsy needle 909. Accordingly, the axial movement of shaft 906 may be used to introduce biopsy needle 909 into tissue, and, conversely, remove biopsy needle 909 from that tissue in order to perform a biopsy. The connection constraint of the needle can be such that the needle rotates with the threaded shaft 906, or such that the rotation and translation of the threaded shaft 906 moves the needle linearly downwards and upwards without rotation.

Needle guide 908 is connected to two rotation tracks 910 and 912 arranged to allow for movement of needle guide 908 along each track and, thereby, rotational orientation of biopsy needle 909 about both the X and Z axes. As illustrated in FIG. 9, track 910 is configured to rotate about the Z-axis (as indicated by arrow 911). Conversely, track 912 is configured to rotate about the X-axis (as indicated by arrow 913). Needle guide 908 is configured to slide along the length of each of tracks 910 and 912. Accordingly, when track 910 rotates about the Z-axis, needle guide 908 slides along the length of track 912, but does not generally change position along the length of track 910. Conversely, when track 912 rotates about the X-axis, needle guide 908 slides back and forth along the length of track 910, but does not generally change position along the length of track 912. Therefore, to rotate biopsy needle 909 about the Z-axis, a magnetic field is applied along the X-axis. Conversely, to rotate needle 909 about the X-axis, a magnetic field is applied along the Z-axis. Because the magnetic fields used to position tracks 912 and 914 are substantially orthogonal to one another, a force applied to move a first one of the tracks, will generally not affect the position of the other track. Accordingly, tracks 912 and 914 can be positioned independently. To allow for high-precision positioning of the tracks, the position of track 912 is fixed (e.g., by a locking or braking mechanism, as described below), while the position of track 910 is adjusted and the position of track 910 is fixed (e.g., by a locking or braking mechanism, as described below), while the position of track 912 is adjusted.

The needle guide 908 is configured to couple to each set of tracks to allow for translation of needle guide 908 along each of tracks 912 and 910 as the tracks are rotated. In one implementation, a first set of guide tracks run along the top surface of track 912 and a similar set of guide tracks run along the underside of track 910. To minimize friction or provide further constraint as tracks 910 and 912 are rotated, plastic (or other MRI-compatible material) ball bearings may be incorporated in at least one of the four points of overlap between recessed, hemisphere guide tracks of track 910 and track 912. In the preferred embodiment, four ball bearings are used to reduce position tolerance through constraints and to reduce the force necessary to reposition needle guide 908 on each of tracks 910 and 912; tracks 910 and 912 do not directly contact each other in this case. Additionally or alternatively, either one or both of the guide tracks of 910 and 912 or, if no guide tracks exist, the surface of tracks 910 and 912, can be made of low-friction material(s), such as Teflon, to further reduce the force necessary to reposition needle guide 908 on each of tracks 910 and 912. Additionally, needle guide 908 may be constructed of a low-friction material, such as Teflon, to further reduce the force necessary to reposition needle guide 908 on each of tracks 910 and 912.

Within device 900, both of tracks 910 and 912 may optionally include additional ferrous materials (e.g., ferrous spheres, not shown) to facilitate movement of each track about its respective axis by the application of an appropriate oriented magnetic field. Additionally or alternatively, the application of a force against the ferrous object 904 disposed within torque arm 902 can be sufficient to reposition each of tracks 910 and 912. Additionally or alternatively, the needle guide 908 may optionally include additional ferrous materials (e.g., ferrous spheres, not shown) to facilitate movement of each track about its respective axis by the application of an appropriate oriented magnetic field.

In an embodiment, each of tracks 910 and 912 are connected to locking or braking mechanisms 916 and 914, respectively, to lock a position of tracks 910 and 912 or to otherwise inhibit movement of tracks 910 and 912. If tracks 910 and 912 were not locked, the actuation of torque arm 902 by an appropriate rotational magnetic field could upset the position of one or more of tracks 910 and 912, which depends on factors such as design and material contact surface coefficients of friction.

Each of braking mechanisms 914 and 916 may be implemented using the same design methodology as that of brake housing 610 (shown in FIGS. 7A, 7B and 7C) incorporating a ferrous object that is held into a first unlocked position by MRI-compatible springs, but that can be moved into a second position (e.g., a locked position) by the application of an appropriately oriented gradient and held in that locked position by the springs.

In device 900, each of braking mechanisms 914 and 916 can be positioned to have different orientations so that a braking gradient application to a first braking mechanism does not affect the other braking mechanism. For example, in one implementation, braking mechanism 914 may be braked by the application of a gradient in the Y-axis direction, while braking mechanism 916 may be locked by the application of a gradient in the Z-axis direction.

Figure 10:
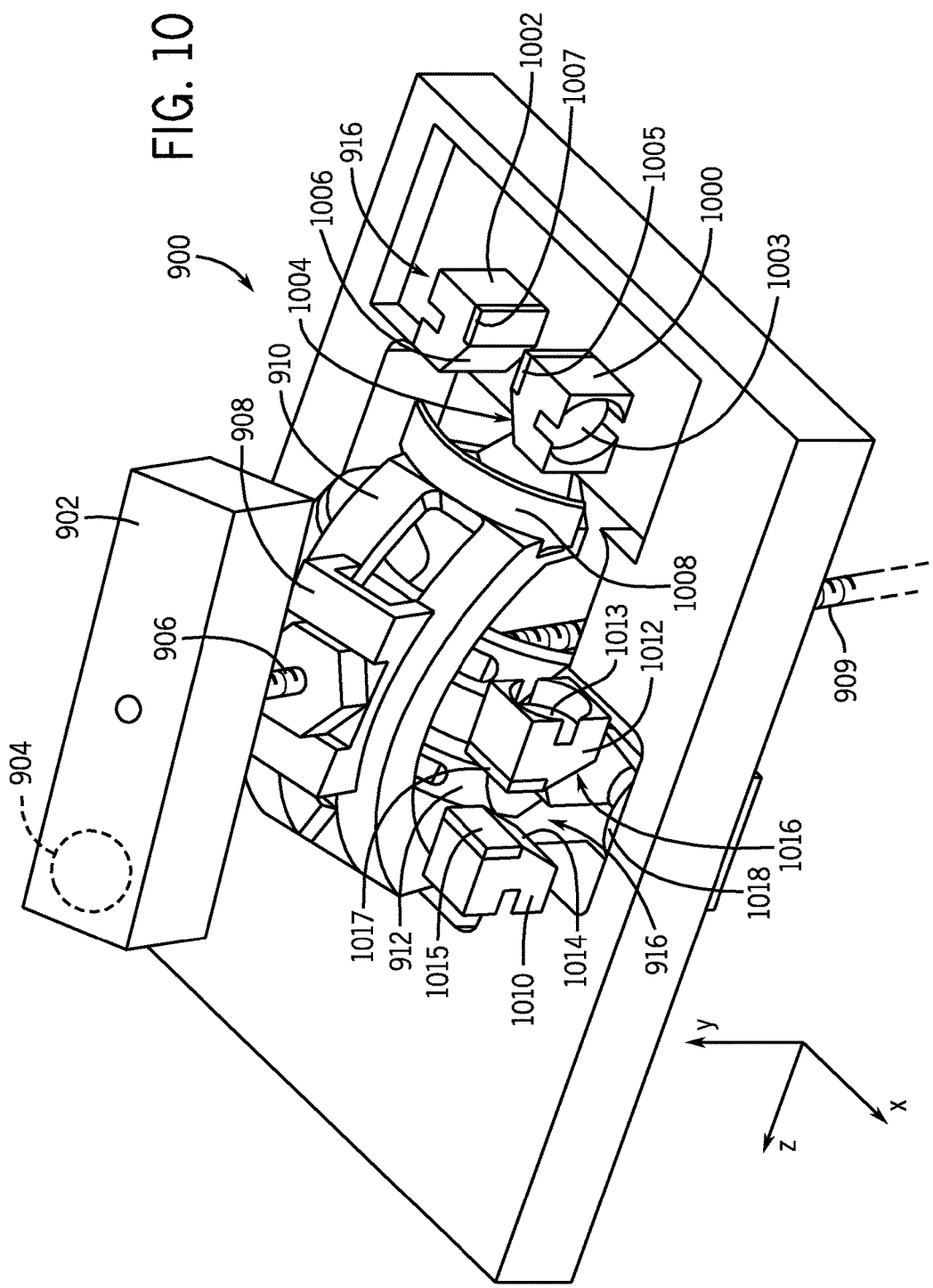
FIG. 10 is an illustration showing detail of the internal structure of braking mechanisms incorporated into the device shown in FIG. 9.

FIG. 10 is an illustration showing detail of the internal structure of braking mechanisms 914 and 916 of device 900. In FIG. 10 only the structure of each braking mechanism is illustrated with the spring and ferrous sphere structure not shown. Braking mechanism 916 includes wedges 1000 and 1002. Each wedge includes a recessed back portion (shown on wedge 1000 as element 1003) sized to receive a spring constructed from an MRI-compatible material. When the springs (not shown) are installed wedges 1000 and 1002 are biased towards one another. A ferrous sphere can then be positioned between each of wedges 1000 and 1002. Wedges 1000 and 1002 include sloped faces 1004 and 1006, respectively, and flat faces 1005 and 1007, respectively. When a ferrous sphere (not shown) is positioned between flat faces 1005 and 1007, the sphere is held in place by the compressive force of the springs. Conversely, when the sphere is positioned between sloped face surfaces 1004 and 1006, the force of the springs biasing wedges 1000 and 1002 causes the sloped surface to push against the ferrous sphere causing the sphere to move in the positive Z-axis direction where it pushes against friction lock surface 1008. Lock surface 1008 is connected to track 910 of device 900 and may include a surface treatment configured to increase the friction between lock surface 1008 and the ferrous sphere of braking mechanism 916. When the ferrous sphere presses against lock surface 1008 with sufficient force, track 910 is locked and can no longer rotate about the Z-axis.

Accordingly, in a default state (with the ferrous sphere positioned between flat faces 1005 and 1007), braking mechanism 916 is unlocked allowing the position of track 910 to be adjusted. To use locking mechanism 916 a linear gradient is applied along the positive Z-axis to pull the ferrous sphere of braking mechanism 916 between the sloped faces 1004 and 1006 of wedges 1000 and 1002, respectively, causing the sphere to be pushed against lock surface 1008. To facilitate movement of wedges 1000 and 1002 within braking mechanism 916, low-friction material, such as Teflon, inserts may be positioned underneath wedges 1000 and 1002 (or on any other contact surfaces) or over the faces of wedges 1000 and 1002 to minimize system friction; a low-friction coating can also be applied to the surfaces of the inserts and/or current material(s). To facilitate movement of the ferrous sphere between the flat faces 1005 and 1007 and/or sloped faces 1004 and 1006 of the wedges 1000 and 1002, low-friction material, such as Teflon, inserts may be applied to the faces of wedges 1000 and 1002 or the surfaces they contact to minimize system friction; a low-friction coating can also be applied to the surfaces of the inserts and/or current material(s).

Braking mechanism 914 includes wedges 1010 and 1012. Each wedge includes a recessed back portion (shown on wedge 1012 as element 1013) sized to receive a spring constructed from an MRI-compatible material. When the springs (not shown) are installed wedges 1010 and 1012 are biased towards one another. A ferrous sphere can then be positioned between each of wedges 1010 and 1012. Wedges 1010 and 1012 include sloped faces 1014 and 1016, respectively, and flat faces 1015 and 1017, respectively. When a ferrous sphere (not shown) is positioned between flat faces 1015 and 1017, the sphere is held in place by the compressive force of the springs. Conversely, when the sphere is positioned between sloped face surfaces 1014 and 1016, the force of the springs biasing wedges 1010 and 1012 causes the sloped surface to push against the ferrous sphere causing the sphere to move in the negative Y-axis direction where is pushes against friction lock surface 1018. Lock surface 1018 is connected to track 912 of device 900 and may include a surface treatment configured to increase the friction between lock surface 1018 and the ferrous sphere of braking mechanism 914. When the ferrous sphere presses against lock surface 1018 with sufficient force, track 912 is locked and can no longer rotate about the X-axis.

Accordingly, in a default state (with the ferrous sphere positioned between flat faces 1015 and 1017), braking mechanism 914 is unlocked allowing the position of track 912 to be adjusted. To lock braking mechanism 914 a linear gradient is applied along the negative Y-axis to pull the ferrous sphere of braking mechanism 914 between the sloped faces 1014 and 1016 of wedges 1010 and 1012, respectively, causing the sphere to be pushed against lock surface 1018. To facilitate movement of wedges 1010 and 1012 within braking mechanism 914, low-friction material, such as Teflon, inserts may be positioned underneath wedges 1010 and 1012 (or on any other contact surfaces) or over the faces of wedges 1010 and 1012 to minimize system friction; a low-friction coating can also be applied to the surfaces of the inserts and/or current material(s). To facilitate movement of the ferrous sphere between the flat faces 1015 and 1017 and/or sloped faces 1014 and 1016 of the wedges 1010 and 1012, low-friction material, such as Teflon, inserts may be applied to the faces of wedges 1010 and 1012 or the surfaces they contact to minimize system friction; a low-friction coating can also be applied to the surfaces of the inserts and/or current material(s).

Accordingly, by selectively applying an appropriate magnetic gradient in either the Z-axis or Y-axis directions, either of braking mechanisms 914 and 916 can be locked to fix the position of tracks 910 and/or 912.

For example, to reposition track 910, braking mechanism 916 is first primed into its unlocked condition with a ferrous sphere being positioned between the flat faces of wedges 1000 and 1002. So positioned, braking mechanism 916 is unlocked and track 910 can be repositioned as appropriate. In one example, track 910 is repositioned by the application of an appropriate magnetic gradient to the ferrous material disposed within torque element 902 (shown in FIG. 9) or other ferrous material disposed within track 910 or needle guide 908, for example. To then lock the position of track 910, a magnetic gradient is applied to braking mechanism 916 to pull the ferrous sphere between the sloped surfaces of wedges 1000 and 1002. In that position, the springs of braking mechanism 916 cause the sphere to be biased against lock surface 1008 of track 910 to prevent movement of track 910. The control algorithm and required forces for both positioning and braking must be designed such that the desired function is achieved.

Figure 12:
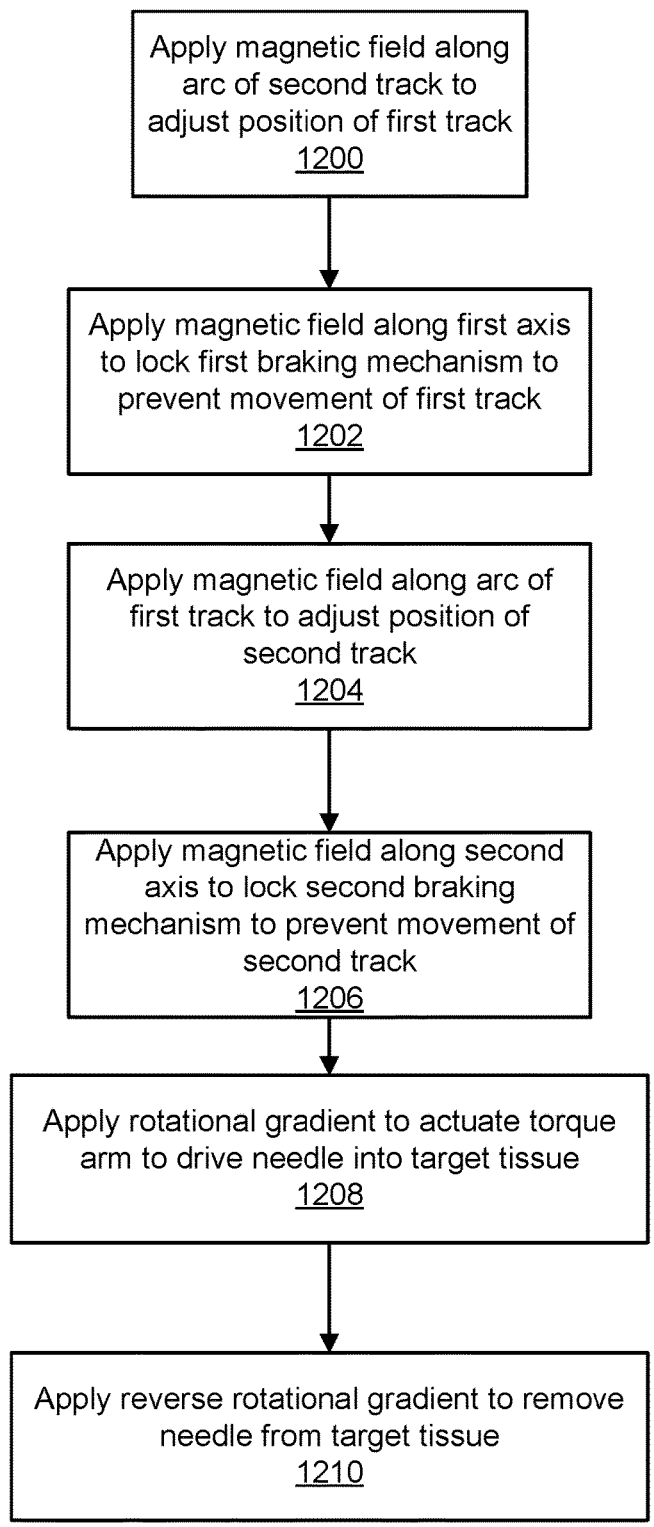
FIG. 12 is a flowchart illustrating an example method of operating the device shown in FIG. 9.

By employing braking mechanisms 914 and 916 to selectively fix the position of each of tracks 910 and 912 and by rotating torque arm 902 to actuate biopsy needle 909 puncture, device 900 can be utilized to execute various functions, such as the performance of a biopsy. In one example use case, device 900 is positioned within an MRI bore. Then, to perform a biopsy using device 900, the following steps may be executed, as illustrated in FIG. 12.

First, in step 1200 a magnetic gradient is applied along the arc of track 912 to rotate biopsy needle 909 about the Z-axis to a preferred orientation. After the needle is appropriately oriented about the Z-axis, a magnetic gradient may be applied in step 1202 along the Z-axis to cause braking mechanism 916 to lock, thereby fixing the position of track 910 or inhibiting movement thereof.

Second, in step 1204, a magnetic gradient is applied along the arc of track 910 to rotate biopsy needle 909 about the X-axis to a preferred orientation. After the needle is appropriate oriented about the X-axis, in step 1206, a magnetic gradient is applied along the Y-axis to cause braking mechanism 914 to lock, thereby fixing the position of track 912 or inhibiting the movement thereof.

Sometimes, the application of the gradient to lock braking mechanism 914 may result in small changes in the position of track 912 as braking mechanism 914 transitions from an unlocked to a locked condition. As such, that deflection should be accounted for in the final positioning of track 912 before braking mechanism 914 is locked. In one implementation, the amount of deflection that may result from the activation of braking mechanism 914 can be pre-calculated and accounted for, or can be determined by a control algorithm that, in turn, compensates for any deflection.

Third, in step 1208, with each of braking mechanisms 914 and 916 in their locked positions, a rotational magnetic field is applied to cause torque arm 902 to rotate thereby deploying needle 909 to the biopsy site. With a sufficiently strong rotational magnetic field, the necessary puncture force for the target tissue is exceeded and the biopsy can be performed.

Fourth, in step 1210, the biopsy is removed by applying the opposite rotational magnetic field to cause torque arm 902 to rotate in the opposite direction causing biopsy needle 909 to be withdrawn from the sample tissue. The connection constraint of the needle 909 can be such that the needle 909 rotates with the threaded shaft 906, or such that the rotation and translation of the threaded shaft 906 moves the needle linearly downwards and upwards without rotation.

Due to the elegance of the various designs and devices described above, scaling the implants/actuators can be readily achieved by resizing the spheres and their non-ferromagnetic "scaffold" to meet the combined force and geometric, design constraints. Spheres of multiple sizes can be used to optimize actuation space. Additionally, materials of higher saturation magnetizations can be used to increase the applied force on smaller spheres. For a certain volume of actuation space, there is a threshold for the amount of force that can be applied with currently available MRI systems and ferromagnetic materials. However, stronger magnetic gradient coils in clinical MRI machines and new materials with higher saturation magnetizations are being developed; both of which will increase the force threshold.

Other actuation mechanisms may also be employed. For example, rather than be constrained within a particular volume, a ferrous sphere may be moved through paths in a non-ferrous scaffold to actuate different components or areas of a device. Braking mechanisms may not be necessary in this case, since the "brake" is applied when the actuation sphere is removed from one actuation position to power the next. For design concepts where brakes are necessary, other braking mechanism designs and schemes can be used, for example: hard-stop braking mechanisms, ratcheting devices, and creating parallel braking mechanism independence through different gradient field, magnitude and/or direction requirements. The final applicable embodiment will be based on the particular application and design parameters. Additionally, the present technology may be partnered in a dependent or independent mechanism with other suitable actuation methods.

Additionally, while spherical ferromagnetic materials have been used for illustration purposes, non-spherical ferromagnetic materials can be used in some applications. For instance, a non-spherical material could "float" in the spherical cavity of the implant/actuator. However, this technique would reduce the efficient use of actuation volume space, and the torque effect of the non-symmetric geometric property may cause undesirable dynamic effects upon device entry into the magnetic field and during actuation. These torque effects are strong enough to easily compromise structural integrity. Thus, non-spherical ferromagnetic geometries would be used in limited circumstances, such as when a beneficial use of the initial dynamic motion from the torque alignment is desired or if spherical shapes of the desired material cannot be manufactured.

As addressed above, cardiac implant applications used to repair the mitral valve can readily benefit from the present invention. The mitral valve is the valve structure that separates the left atrium from the left ventricle. It opens during ventricular diastole and closes during ventricular systole, when the left ventricle pumps blood to the rest of the body. The valve and subvalvular structure provide the mechanisms for proper function. The valve consists of two leaflets, the anterior and posterior leaflets, which are connected to the heart wall at the mitral valve annulus. These leaflets open to let blood flow through, and then coapt to provide valve closure. Preventing valve inversion and causing coaptation, chordae attach the leaflet edges to two papillary muscles, which are attached to the wall of the left ventricle; this apparatus makes up the subvalvular structure.

Mitral valve prolapse (MVP) is the condition in which the two leaflets of the mitral valve do not coapt properly, causing a leaky (regurgitant) valve. MVP is the most common valvular disorder, affecting nearly 6% of the U.S. population. One surgical procedure to repair MVP is to implant artificial PTFE (i.e., Teflon) chords at the prolapsed portion of the valve to properly approximate the leaflet edge to the papillary muscle. Typically, the artificial chords replace either broken or stretched natural chordae tendinae that once approximated these two tissue structures for proper leaflet coaptation.

Currently, artificial chords are implanted during open heart procedures. This leads to a variety of complications, including the uncertainty of proper chord length. Once the chords are installed, proper leaflet coaptation is verified by pressurizing the left ventricle with saline and observing the valve for leaks. Although this assures proper coaptation during installation, the heart geometry and function are vastly different once the patient is off-bypass. Therefore, this type of repair does not guarantee a perfect coaptation, yet is one of the best-in-practice repairs that exist today.

The chord implants present additional, post surgical issues. As the valve disease process continues, MVP may reoccur due to changes in tissue properties, which cause the proper chord length for coaptation to vary overtime. However, an additional open heart procedure is often not advisable, and the patient must live with any symptoms caused by mild regurgitation.

The potential of adjustable chords is recognized in U.S. Patent Application Publication No. 2008/0228272 and is incorporated herein by reference. However, the technology relies on shape memory alloys to achieve adjustments. This technology has many foreseen complications in artificial chord applications, as shape memory alloys rely on the application of controlled heat. Not only is applied heat a potential danger in cardiac applications, but controlling the temperature in a dynamic, fluid environment will lead to complex systems. Additionally, shape memory alloys are typically adjustable only to predefined, discrete positions.

By utilizing the dexterity of the magnetic fields previously discussed, mechanical mechanisms can be used to achieve the desired adjustments. The RF and/or magnetic gradient fields can produce the forces for adjustment and create chord lengths that can be percutaneously fine-tuned. One possible adjustable chord design is to incorporate a ratcheting mechanism along the length of the chord made with nonferrous materials. In cardiac applications, the required adjustment force can be minimized, if necessary, by applying intermittent adjustments in unison with the patient's gate cycle; therefore, adjustments can be made, for example, when the chords are under their lowest loads. Additionally, this new technological application of MRI can be applied to design many other morphable implants that can actuate within the available, design-based force range.

The foregoing discussion is directed to macroscopic ferromagnetic materials. However, in some instances, nano-spheres can also be used for actuation purposes. One benefit of using nano-spheres is that they often present superparamagnetic properties. Therefore, upon removal of the spheres from a magnetic field, they do not usually retain a magnetization. This is beneficial in circumstances were a retention of magnetization would be detrimental, and methods to eliminate or minimize any retained magnetization are not feasible. If a design can tolerate the loss of magnetic actuation density due to the required spacing of multiple nano-spheres, then it may benefit from the inherent properties of nano-spheres.

Again, however, it is noted that cavity spacing plays an important role in actuation and, differences in sphere size, particularly, an extremely large difference in size, such as between nano- and macro-spheres, substantially changes these considerations and constraints. In particular, if separate magnetic cavities exist and the magnetic cavities are "too close together," no actuation will occur. Of course, the concept of "close" is relative and differs substantially based on the scale of the material components and their material properties. Using common MRI gradient fields, the spacing may need to be, for example, on the order of approximately 5 times the radius of the sphere for desired actuation to be achieved. Therefore, at the nano-scale, the coating thickness or other spacing method to maintain a certain separation is important (if the spheres are embedded in the scaffold to act as separate actuation volumes), and the summation of all the magnetic forces is then used for actuation of the scaffold body. A reduction in magnetic density must be acceptable when using independent magnetic nano-spheres versus a solid sphere volume. This is substantially different from considerations used with respect to robotic drug-delivery applications using magnetic nano-spheres, where the spheres rely on physical movement with respect to each other in order to achieve magnetic interactions with each other, in order to produce higher magnetic forces, much more than of a single particle, to overcome the high forces of the bloodstream. Complex control methods are currently being developed to regulate these particle interactions. Therefore, for robotic drug delivery, the particle separation must not be large enough to eliminate their magnetic interaction for actuation to occur.

The fundamental concepts described in above sections differ when applied to magnetically isotropic materials. With isotropy, the magnetization vector of each sphere has no fixed alignment due to anisotropy, and therefore, it is free to rotate in the ferromagnetic material. Therefore, the spheres (or other shapes, if shape anisotropy is overcome) can be fully constrained in their scaffold material and need not overcome the anisotropic torque issues addressed in the present invention by providing the macro-spheres with a "free-to-rotate environment." This allows the potential for simplified manufacturing and assembly. For example, magnetically isotropic nano-spheres can be previously mixed into a plastic resin and injection molded. A coating can be previously placed on the spheres to maintain their proper spacing. Additionally, isotropic macro-spheres can easily be imbedded into a plastic prior to its solidification. Limited isotropic magnetic materials have been discovered in the literature from the nano-scale to the macro-scale. The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
   a magnet system configured to generate a polarizing magnetic field about at least a portion of a subject arranged in the MRI system, wherein subject includes a non-ferromagnetic medical implant arranged therein and including at least one cavity and at least one ferromagnetic or ferrimagnetic material arranged within the at least one cavity, wherein the ferromagnetic or ferrimagnetic material formed as a sphere that is substantially free to rotate within the at least one cavity;
   a plurality of gradient coils configured to apply a gradient field to the polarizing magnetic field;
   a radio frequency (RF) system configured to apply an excitation field to the subject and acquire MR image data therefrom;
   a computer programmed to carry out the steps of:
      (a) performing a medical imaging process to acquire MR image data to determine therefrom at least one of a location and an orientation of the non-ferromagnetic medical implant arranged within the subject; and
      (b) controlling the plurality of gradient coils and RF system to magnetically induce forces on the at least one ferromagnetic or ferrimagnetic material arranged within the at least one cavity to move the at least one ferromagnetic or ferrimagnetic material in the cavity and apply the induced forces to the non-ferromagnetic medical implant to effectuate a non-invasive, indirect, in vivo positional manipulation of the non-ferromagnetic medical implant.

2. The system of claim 1 wherein the computer is further programmed to repeat steps (a) and (b) and, after iterations of steps (a) and (b) is further programmed to compare at least one of a current location of the non-ferromagnetic medical implant, a current orientation of the non-ferromagnetic medical implant, and a current physiological state determined from the acquired MR image data to at least one of a desired location of the non-ferromagnetic medical implant, a desired orientation of the non-ferromagnetic medical implant, and a desired physiological outcome.

3. The system of claim 1 wherein the at least one ferromagnetic or ferrimagnetic material is formed as a sphere that is substantially free to rotate within the at least one cavity to effectuate in vivo positional manipulation of the non-ferromagnetic implant irrespective of whether movement of the at least one ferromagnetic or ferrimagnetic material in the cavity is rotational or sliding.

4. The system of claim 1 wherein the at least one ferromagnetic or ferrimagnetic material is formed as a macroscopic sphere.

5. The system of claim 1 wherein the non-ferromagnetic implant includes at least one of an orthopedic implant, an artificial heart valve, an annuloplasty ring associated with a heart implant, an artificial chord associated with a heart implant, a laproscopic band, and a pediatric implant.

6. A method of non-invasively manipulating a medical implant arranged within a subject, the method comprising the steps of:
arranging a subject having a non-ferromagnetic medical implant arranged therein within a system having a static magnetic field and a plurality of adjustable magnetic fields, wherein the non-ferromagnetic medical implant includes at least one cavity and at least one ferromagnetic or ferrimagnetic material arranged within the at least one cavity that is formed as a sphere that is substantially free to rotate within the at least one cavity; and
controlling the plurality of adjustable magnetic fields of the system to magnetically induce forces on the at least one ferromagnetic or ferrimagnetic material arranged within the at least one cavity that cause the at least one ferromagnetic or ferrimagnetic material to push against the non-ferromagnetic medical implant to effectuate an induced, non-invasive, in vivo positional manipulation of the non-ferromagnetic medical implant.

7. The method of claim 6 wherein the at least one ferromagnetic or ferrimagnetic material is formed as a sphere that is substantially free to rotate within the at least one cavity to effectuate the induced, in vivo positional manipulation of the non-ferromagnetic implant irrespective whether motion of the at least one ferromagnetic or ferrimagnetic material in the cavity is rotational or sliding.

8. The method of claim 6 further comprising performing a magnetic resonance imaging procedure in conjunction with the step of controlling the plurality of adjustable magnetic fields of the system.

9. The method of claim 6 wherein the at least one ferromagnetic or ferrimagnetic material is formed as a macroscopic sphere.

10. The method of claim 6 wherein the non-ferromagnetic implant includes at least one of an orthopedic implant, an artificial heart valve, an annuloplasty ring associated with a heart implant, an artificial chord associated with a heart implant, a laproscopic band, and a pediatric implant.

11. A method of manipulating a medical device to perform a medical procedure, the method comprising the steps of:
arranging a medical device within a system having a static magnetic field and a plurality of adjustable magnetic fields, wherein the medical device is configured to interact with a subject and includes at least one cavity and at least one ferromagnetic or ferrimagnetic material formed as a sphere and arranged within the at least one cavity such that the sphere is free to rotate within the at least one cavity; and
controlling the plurality of adjustable magnetic fields of the system to magnetically induce forces on the at least one ferromagnetic or ferrimagnetic material arranged within the at least one cavity to apply the induced forces to the medical device through movement of the sphere against the cavity to move a position of the medical device relative to the subject and effectuate a medical procedure on the subject.

12. The method of claim 11 wherein the sphere is free to rotate or slide within the at least one cavity to move the position of the medical device relative to the subject.

13. The method of claim 11 further comprising performing a magnetic resonance imaging procedure in conjunction with the step of controlling the plurality of adjustable magnetic fields of the system.

14. The method of claim 11 wherein the at least one ferromagnetic or ferrimagnetic material is formed as a macroscopic sphere.

15. The method of claim 11 wherein the medical device is a robotic interventional device.

16. A method of manipulating a device arranged within a magnetic resonance imaging (MRI) system, the method comprising the steps of:
arranging a device within a static magnetic field and a plurality of adjustable magnetic fields of an MRI system, wherein the device is substantially formed of non-ferromagnetic materials and includes at least one cavity and at least one ferromagnetic or ferrimagnetic material arranged within the at least one cavity; and
controlling the plurality of adjustable magnetic fields of the MRI system to induce magnetic forces on the at least one ferromagnetic or ferrimagnetic material arranged within the at least one cavity to thereby apply the induced magnetic forces to a wall of the cavity to effectuate indirect positional manipulation of the device using the magnetic forces induced by the MRI system.

17. The method of claim 16 wherein the at least one ferromagnetic or ferrimagnetic material is formed as a sphere that is substantially free to rotate within the at least one cavity.

18. The method of claim 16 further comprising performing a magnetic resonance imaging procedure in conjunction with the step of controlling the plurality of adjustable magnetic fields of the system.

19. The method of claim 16 wherein the at least one ferromagnetic or ferrimagnetic material is formed as a macroscopic sphere.

20. The method of claim 16 wherein the device is a robotic interventional device.

* * * * *